United States Patent [19]

Heller et al.

[11] Patent Number: 4,826,977

[45] Date of Patent: May 2, 1989

[54] PHOTOCHROMIC SPIROPYRAN COMPOUNDS

[75] Inventors: Harry G. Heller, Llandaff, Wales; Stephen N. Oliver, Felixstowe, England; John Whittall, Caerphilly, Wales; Ian Tomlinson, Midland, Mich.

[73] Assignee: The Plessey Company plc, Ilfor, England

[21] Appl. No.: 50,101

[22] Filed: May 15, 1987

[30] Foreign Application Priority Data

May 15, 1986 [GB] United Kingdom ................ 8611837

[51] Int. Cl.[4] .................... C07D 265/00; G03C 1/733; G02B 27/00

[52] U.S. Cl. ...................................... 544/70; 548/407; 549/24; 549/26; 549/42; 549/43; 549/44; 549/48; 549/264; 549/331; 549/345; 252/586

[58] Field of Search .................... 544/70, 71; 548/407; 549/24, 26, 42, 43, 44, 48, 264, 331, 345; 252/586

[56] References Cited

U.S. PATENT DOCUMENTS

| | | | |
|---|---|---|---|
| 2,542,386 | 2/1951 | Beakie | 18/58 |
| 3,231,584 | 1/1966 | Berman | 260/319 |
| 3,404,861 | 2/1966 | Ewer | 249/187 |
| 3,567,605 | 3/1971 | Becker | 204/158 |
| 3,627,690 | 12/1971 | Casella | 252/586 |
| 3,944,637 | 3/1976 | Bond et al. | 264/1 |

FOREIGN PATENT DOCUMENTS 0246114  11/1987  European Pat. Off. .
2146327   4/1985  United Kingdom .

OTHER PUBLICATIONS

"Photochemical . . . Chromenes", J. Org. Chem., vol. 40, No. 8, 1975, p. 1142, Padwa.

Primary Examiner—Matthew A. Thexton
Assistant Examiner—Catherine S. Kilby
Attorney, Agent, or Firm—Sughrue, Mion, Zinn, Macpeak & Seas

[57] ABSTRACT

A series of novel photochromic spiropyrans are disclosed in which a spiro-adamantane group is introduced into the 2-position of the benzopyran or naphthopyran ring. The spiropyran compounds of the invention exhibit heliochromic properties, i.e. they color in sunlight and fade rapidly at ambient temperatures in the absence of U.V. light, making them good candidates for use in the manufacture of sunglasses. The invention includes lenses which darken in sunlight and incorporate the novel spiropyrans and a process for the preparation of the spiropyran compounds.

11 Claims, 5 Drawing Sheets

Qualitative spectra of HC1, HC7, and 4-phenyl HC7 in 1,2-dichloromethane.

Qualitative spectra of HC1, HC7, and 4 phenyl HC7 in 1,2-dichloromethane.

Qualitative spectra of HC57 in chloroform before and after exposure to light from a flashgun.

Qualitative spectra of 6-p-methoxyphenyl-9-methoxy HC7 in toluene before and after exposure to light from a flashgun.

(Example 13)

Qualitative spectra of 6-chloro-HC7 in toluene before and after exposure to light from a flashgun. (Example 14)

PHOTOCHROMIC SPIROPYRAN COMPOUNDS

BACKGROUND OF THE INVENTION

This invention relates to photochromic spiropyrans and in particular is concerned with photochromic spiro-benzopyrans and spiro-naphthopyrans which are resistant to fatigue reactions.

DESCRIPTION OF THE PRIOR ART

U.S. Pat. No. 3,567,605 (Becker) describes a series of pyran derivatives, including certain benzopyrans and naphthopyrans, but not spiro-compounds, which exhibit photochromic properties. These compounds can be regarded as derivatives of chromene. Typically, the compounds undergo a colourless to yellow-orange change on irradiation by U.V. light. However, the observation of this behaviour by Becker was restricted to temperatures below about −40° C. and Becker reported that the colour change was reversed when the temperature was raised to a temperature in the range of −10° C. to 0° C.

SUMMARY OF THE INVENTION

We have now discovered that a remarkable improvement in the properties of known photochromic chromenes can be secured by introducing a spiro-adamantane group into the 2-position of a benzopyran or naphthopyran ring. In particular, the resulting spiro-adamantane compounds exhibit photochromic behaviour at higher temperatures than those noted by Becker and also show a marked freedom from fatigue or irreversible side reactions.

The spiro-pyrans of the present invention can be represented in general terms by the following general formulae (I), (II) and (III), in which formula (I) represents the 2H- benzopyran series and formulae (II) and (III) represent the isomeric naphthopyran series.

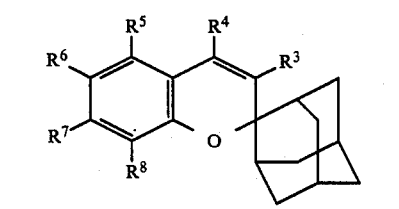
(I)

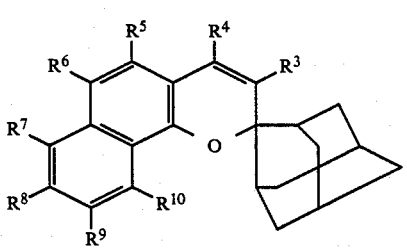
(II)

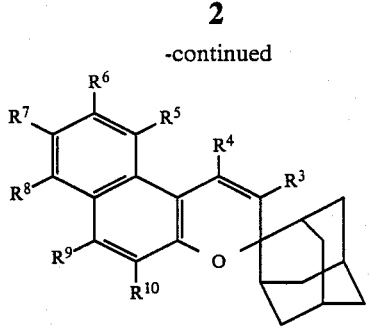
(III)

A wide variety of substituents are possible in the benzopyran or napthopyran rings. For example, the rings can be substituted in the positions represented by $R_3$ to $R_8$ (or $R_3$ to $R_{10}$) with alkyl, aryl (including substituted phenyl, e.g. alkoxyphenyl and halophenyl), alkoxy, hydroxy, alkyl or dialkylamino (e.g. dimethylamino), alkylamino-phenyl, halogen or heterocylic groups, with the proviso that hydroxy or alkoxy or alkyl- or dialkylamino may not be a substituent in the $R_3$ or $R_4$ position. Preferred substituents are lower alkyl (e.g. methyl or ethyl), chlorine, bromine, hydroxy, phenyl, methoxy, or methoxy phenyl groups. It is also possible to produce related series of compounds in which the basic benzopyran or naphthopyran nuclei are annelated with aryl or heterocyclic rings, such as a thiopene or furan ring. Such compounds will be described in more detail subsequently herein.

In addition to its beneficial effect in reducing fatigue reactions, the introduction of the spiro-2adamantane group tends to cause an increase in the quantum yield for colouring in the U.V. region, whilst providing a fast thermal fade at ambient temperature. These properties make them good candidates for use in sunglasses, although other photochromic applications are possible, such as those mentioned by Becker in the above cited U.S. Patent.

BRIEF DESCRIPTION OF THE FIGURES

In the following description, reference will be made to the accompanying FIGS. 1 to 3 and the accompanying sheets of formulae drawings.

In the Figures.

DETAILED DESCRIPTION OF THE INVENTION

Figure 1:
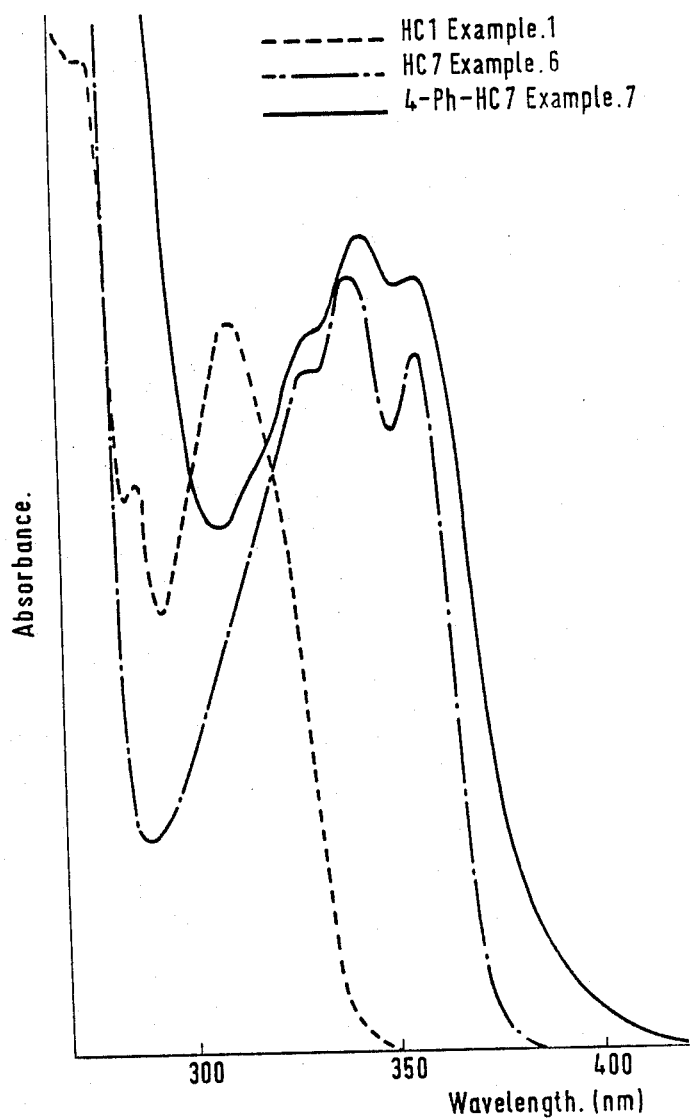
FIG. 1 shows the absorption spectra of the compounds obtained in Examples 1, 6 & 7 in their colourless states.

In general, the spiropyrans represented by formula (I) exhibit colour changes from colourless to yellow-orange in unfiltered sunlight. They tend to show a surface colouring effect in unstirred solutions or a surface colouring effect when incorporated in a plastics matrix. The later phenomenon arises because the coloured forms tend to absorb strongly in the near ultra-violet region (above about 330 nm). As a consequence, the coloured form in a surface layer absorbs the incident U.V. light and prevents it penetrating and colouring spirobenzopyrans within the interior.

Benzannelation causes a marked bathochromic shift of the U.V. absorption band in the near ultra violet of the colourless form. Thus the naphthopyrans are more sensitive to unfiltered sunlight because of their greater cross-capture of U.V. light in sunlight and reduced internal filter effect which is due to the relatively weaker absorption of U.V. light by the coloured form. Coloured forms of the naphthopyrans are yellow to orange/red. These naphthopyrans are soluble in plastic materials traditionally used for plastic lenses, such as methyl methacrylate, polycarbonates and C-39 plastics (see U.S. Pat. No. 2,542,386). Compounds which are currently preferred for use in sunglasses are those represented by the general formula (II) above. These compounds exhibit "heliochromic" properties to a marked degree. The term "heliochromic" is used to describe the following desirable photochromic properties for an effective agent to be used in photoreactive lenses, viz:

(a) a high quantum yield for colouring in the near ultra-violet.

(b) a low quantum yield for bleaching with visible light.

(c) a fast thermal fade at ambient temperatures.

In addition, these properties are desirably retained in the conventional rigid plastics used for opthalmic and plano lenses.

In order to facilitate identification of the photochromic compounds described in this specification, the following code will be used hereinafter to designate the basic chromene (HC1, HC5 etc) in which the number indicates the first benzannelated carbon.

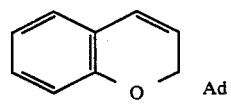
HC1

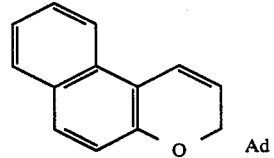
HC5

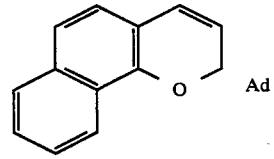
HC7

For sunglass applications, we currently prefer adamantane-2-spiro-2¹[2H-1,2b-napthopyran] and its derivatives (the HC7 series). The structural formula of these compounds are given in sheet 1 of the attached formulae drawings, formula (V). Examples of specific derivatives are those in which $R^6$ in formula (V), sheet 1—represents lower alkyl e.g. methyl, chlorine, bromine, phenyl, hydroxy, methoxy or methoxy phenyl. Compounds of formula (V) may also be substituted in other positions and the nature of these substituents has little effect on the photochromic behaviour of the compounds, except in the 3 and 4 positions where certain substituents can cause steric interactions in the coloured form produced on ring-opening, as discussed below.

On irradiation of compounds of formula (V) with U.V. light, the pyran ring opens reversibly at the carbon-oxygen bond between the spiro carbon and the ring oxygen, to form cis and trans structures (VI) and (VII)

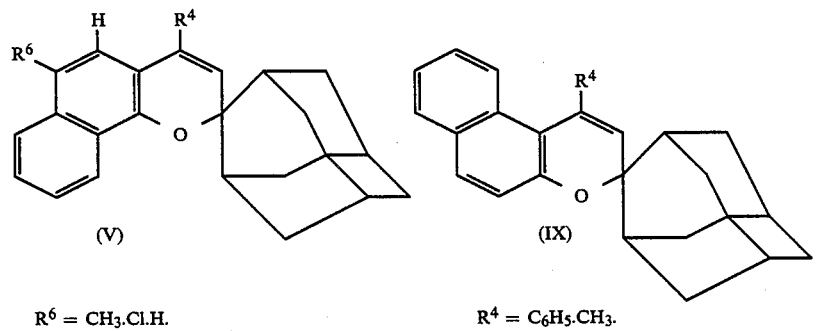

(V)

$R^6$ = CH₃.Cl.H.
OH or OCH₃

(IX)

$R^4$ = C₆H₅.CH₃.
Br or H

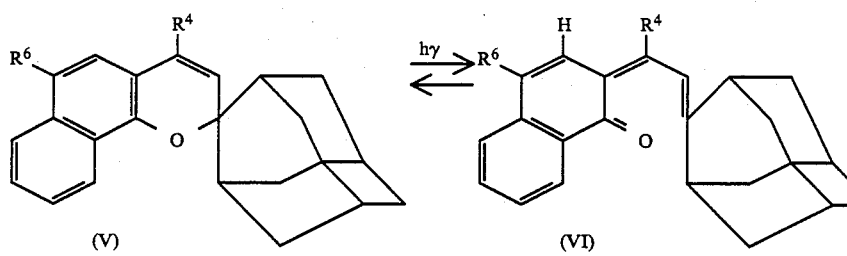

(V)             (VI)

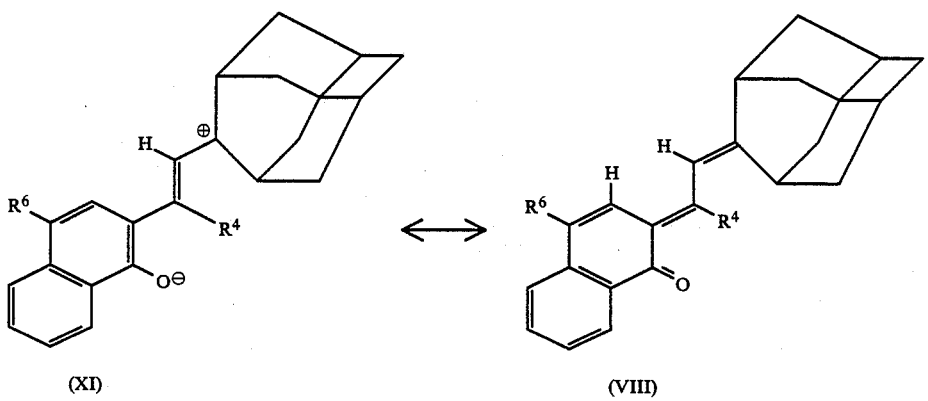

(XI)             (VIII)

The ring-opened structure can be represented as a polar state (XI) having a conjugated chain extending from the adamantane ring to the oxygen. The formation of this polar conjugated structure is believed to be responsible for the colouring of the compounds on exposure to U.V. light.

Compounds of formula (V) in undergo a colour change from colourless to yellow on exposure to U.V. light. A bathochromic shift in the absorption spectra of the coloured form will occur if the chromophore is lengthened. This can be achieved, for example, by introducing a p-methoxyphenyl group in the $R^6$ position in formula (V). The structure of this compound (formula 9)

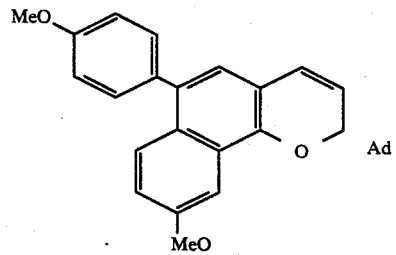

(9)

in which C⌒Ad represents an adamantylidene group. In this case, in the coloured, excited state, the electron releasing p-methoxyphenyl group brings about electron migration to the adamantylidene group resulting in a much longer conjugated system extending between the dipoles, (see formula 9A). Consequently, the compound 9, as expected, produces a red coloured form on irradiation. The methoxy group in the 9 position in the naphthopyran has no marked effect on the colour and is present as a substituent because of the method of preparation. It will be appreciated that other electron releasing groups could be introduced into the basic nucleus to produce similar electron migrations, e.g. an alkylamino, aminophenyl, or an alkyl- or dialkyl- aminophenyl group could be introduced in the 6 position.

Benzannelation, on the other hand, causes a hypsochromic shift in the absorption spectra of the coloured form. This is illustrated by a comparison between the absorption spectra of the HC1 and HC7 series of compounds. Thus, HC1 itself, has a yellow/orange coloured form while HC7 is yellow when irradiated. Similarly, 6-p-methoxyphenyl-9-methoxy-HC7 has an adsorption maximum at 488 nm (red) while the absorption maximum of the corresponding 6-p-methoxyphenyl-HC1 is at 512 nm (red-purple).

Another approach to obtaining different absorption characteristics in the coloured forms is to annelate the basic nuclei with heterocyclic rings, especially an oxygen or sulphur-containing five or six-membered ring. For example, the compound (3)

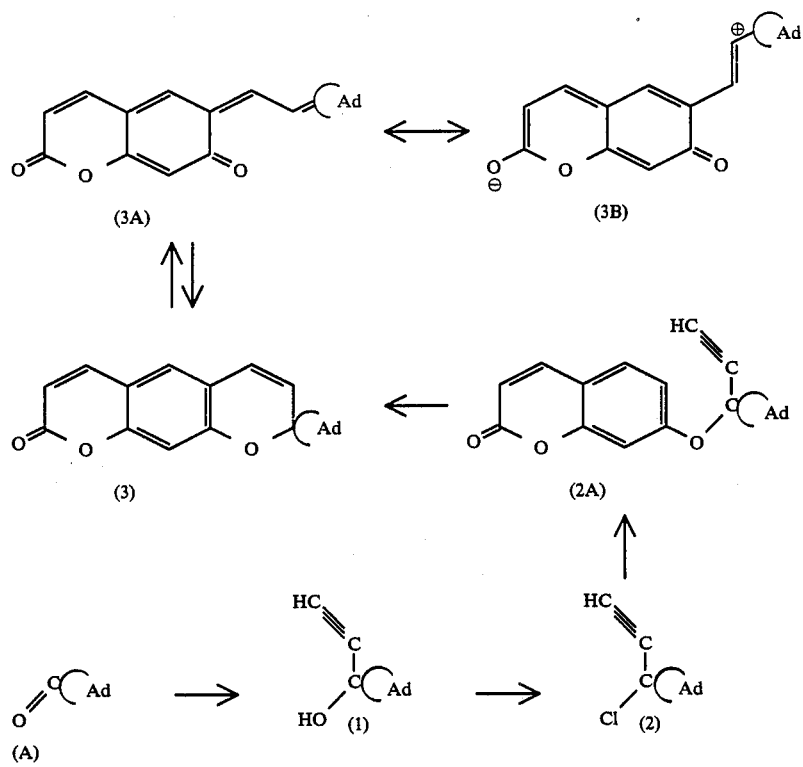

can be regarded as a lactone derivative of HCl having a fused pyrone ring in the 6,7 positions. This compound, on irradiation, is capable of existing in a polar state in which a conjugated chain extends from a negative charge on the carbonyl oxygen of the lactone ring to the spiro carbon of the adamantylidene ring. See structures 3A and 3B. As a consequence of this extended chromophore, the compound (3) has an absorption maximum in the purple/blue range. Compound (3) can be prepared from 7-hydroxy coumarin and ethynyl-adamantanyl chloride.

Conventional photoreactive inorganic glass lenses containing silver halide particles darken to a grey or brown colour in sunlight. In order to duplicate this colour change in a plastics lens using photochromic chromenes described in this application, the compounds can be mixed or used in conjunction to produce the desired shade on exposure to U.V. light. For example, a compound which colours to yellow can be blended with a compound which colours to purple to produce a brown shade. Similarly, a compound which is yellow in its coloured state will produce a grey shade in conjunction with a blue colouring compound.

Many of the heliochromic compounds described in our U.K. patent application No. 8422200 (publication No. 2146327) colour to purple or blue and these compounds can be used in admixture with or in conjunction with yellow-colouring heliochromic compounds described in this application.

The photochromic compounds, when used in sunglass applications, must be capable of fading to the colourless state at normal ambient temperatures when not exposed to U.V. light. It is not necessary for the photochromic compounds, where two or more are used together, to fade at the same rate. It may be considered desirable, for example, for the more deeply coloured compound to fade more rapidly.

The fade rate of the compounds of general formula (II) above can be modified, for example, by introducing substituent groups in the $R^4$ position. For example, if bulky groups are present in this position the change between the structural forms represented by formula (VI) and (VII) above, will be hindered and the fade rate correspondingly increased. Modification of the structure of a particular photochromic compound may be desirable in certain cases in order to ensure that the colour fades rapidly enough when moving from bright sunlight to shaded conditions. Examples of suitable substituents in for $R^4$ is methyl, phenyl, paramethoxyphenyl and halogen. Preferably, $R^3$ is hydrogen. The corresponding phenanthrene compounds also exhibit an increased fade rate.

Benzannelation of the chromene can influence both the colour change on irradiation, as well as the fade rate of the coloured form. This is illustrated by the behaviour of the compound HC57,

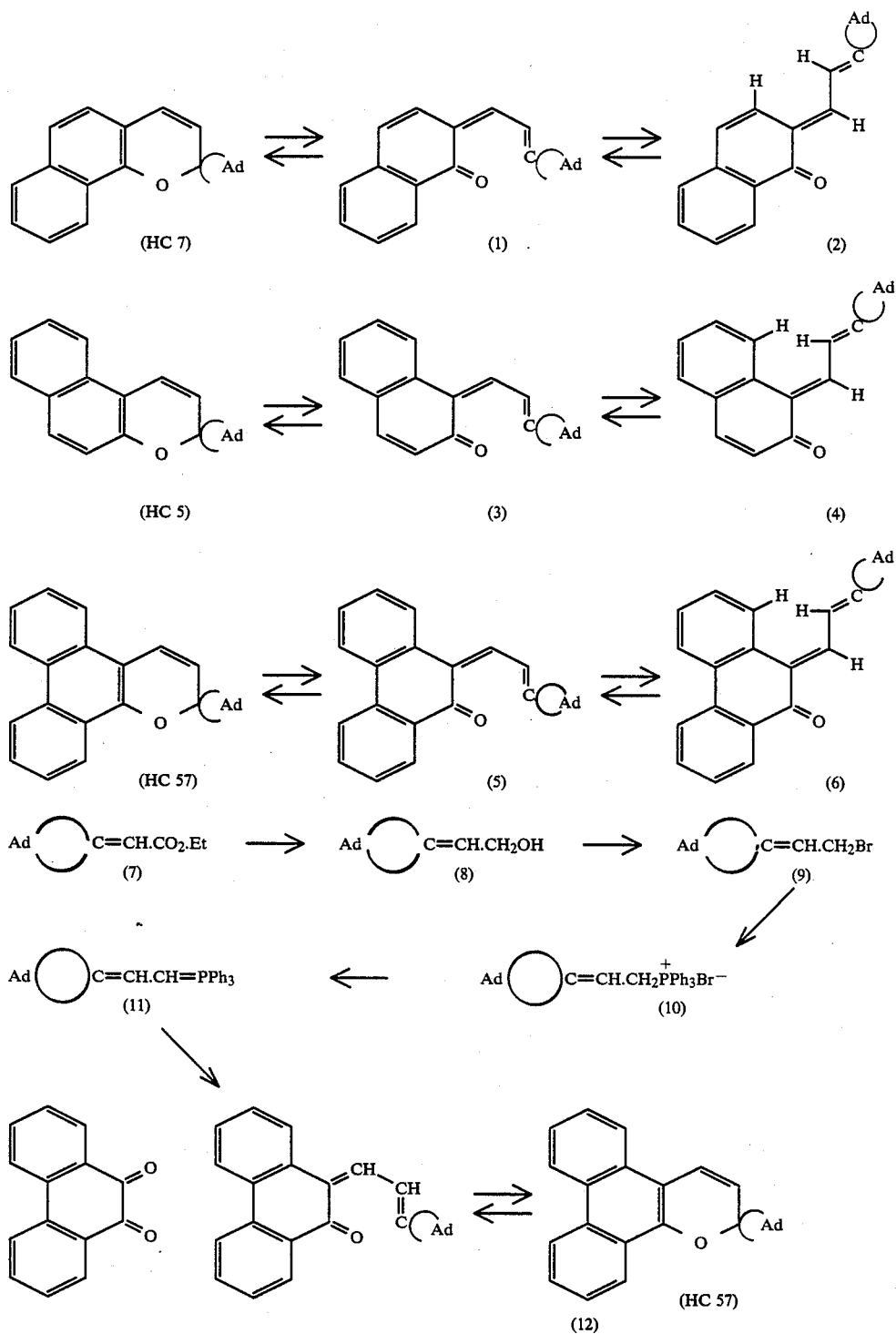

which can be regarded as HC7 benzannelated in the 5, 6 positions. HC7 has two fade rates. A fast fade rate which is attributable to the cisoid form (1) and a slower rate attributable to the transoid form (2). Similarly, HC5 shows two fade rates which are both faster than the fade rate of the transoid form of HC7 (2).

The explanation seems to be that the transoid form of HC5 (4) is subjected to greater steric interactions than the transoid form of HC7 (2). Consequently, there is a loss of thermodynamic stability in the transoid form and the cisoid isomer is preferred.

In the case of HC57, the benzannelation increases the stability of the coloured form but this is partly offset by steric interactions in the transoid form HC57 (6), similar to those of HC5 (4). As a result, the fade rates of the coloured form of HC57 lie between those of HC5 and HC7. Benzannelation in HC57 produced, as expected, a hypsochromic shift in the absorption spectra of the coloured form.

Heliochromic spiropyrans in accordance with the present invention are sufficiently stable to be capable of incorporation in conventional plastics lens material such as acrylic materials, without appreciable degradation.

The heliochromic spiropyrans of this invention can be added to a polymerisation mixture from which plastics lenses are intended to be produced. For example, in one test methyl methacrylate (5 ccm) containing the compound of formula (V) ($R^6$=H)

types of plastic lenses; these are essentially polycarbonate and alkyl acrylate and methacrylate lenses. The most commonly used material for plastic lenses is diethylene glycol bis (allyl carbonate) usually known as CR-39 (CR-39 is a trade mark of P.P.G. Ltd.). Methods of manufacturing plastic lenses are described for example in U.S. Pat. Nos. 3,944,637, 2,542,386 and 3,4094,861, the disclosure of which are incorporated herein by reference.

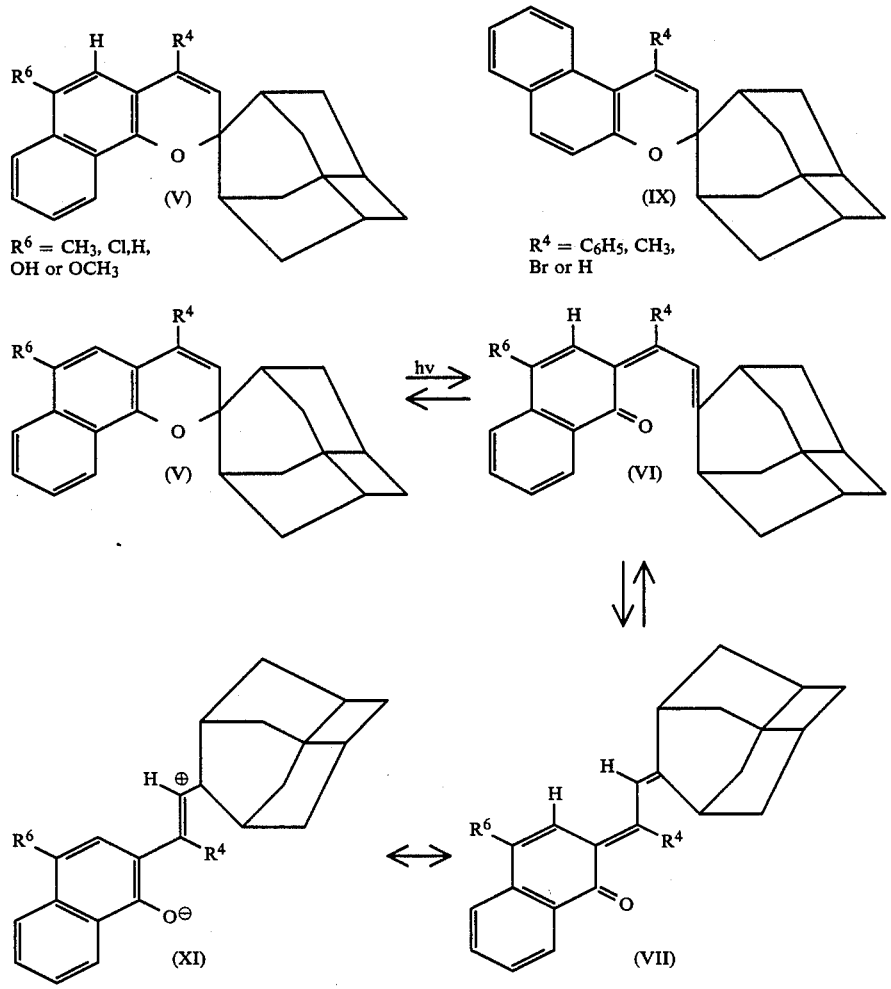

(0.15 g) and benzoyl peroxide (0.15 g) was polymerised by heating at 100° C. for 30 minutes. The resulting polymer was found to be heliochromic, which indicates that the heliochromes are able to survive the conditions prevailing in peroxidecatalysed polymerisations.

The heliochromic compound need not be incorporated in the lens material. It is also possible to apply a coating of the heliochromic compound to the preformed lens or to imbibe the lens in a solution of the compound. Where more than one heliochromic compound is employed, one compound may be incorporated in the lens polymer and a second compound applied subsequently to the lens after manufacture. Alternatively, two or more heliochromic compounds may be imbibed or otherwise incorporated into the preformed lens.

Generally it is envisaged that the compounds of this invention will be used to render photoreactive the usual A General Procedure for the Synthesis of Adamantane spiropyrans The following procedure can be followed to prepare spiro pyrans in accordance with the invention. It will be appreciated that chromene is an alternative name for benzopyran. Thus, 2H-chromene is an alternative name for 2H-1-benzopyran.

3.1a Condensation

Adamantanone (1 mole), the o-hydroxyacetophenone (1.1 mole) and a cyclic secondary amine (1.2 mole) are dissolved in toluene (1 cm³ for each g of reactant) and boiled (5–24 hours) until water is no longer produced. The water is removed as an azeotrope with toluene using a Dean and Stark apparatus. Toluene is then removed under reduced pressure and the residual enamine is recrystallised from acetone or ethanol.

3.1b Hydrolysis

The enamine is dissolved in the minimum quantity of boiling methanol and c. hydrochloric acid (1 cm³ for every 10 g of enamine) is added. On standing, the chromanone sometimes crystallises out. If the yield of chromanone is low, the solution is heated to boiling and hot water is added until the solution becomes turbid. On cooling, the chromanone separates.

3.1c Reduction

Sodium borohydride (1 g per 2.5 g of chromanone) is added in small portions to the chromanone in methanol (3 cm³ per g of chromanone). When the addition is complete, the reaction mixture is boiled (2 hours) and methanol removed under reduced pressure. The residue is added to water, extracted with chloroform, dried (MgSO₄) and solvent removed, leaving the crude chromanol.

3.1d Dehydration

Solvated copper sulphate, CuSO₄0.5H₂O is heated strongly in a boiling tube with a bunsen burner until no more water is evolved. The resulting anhydrous copper sulphate is admixed with the chromanol(1g per 2 g of chromanol) in a flask and heated with a bunsen burner until the organic compound melts. On cooling, the reaction mixture is extracted with chloroform, solvent is removed and the residual chromene is recrystallised from acetone or ethanol. A decolourisation with activated charcoal may be necessary.

Alternatively, the compounds of the present invention may be prepared by a novel process based on the Claisen rearrangement. This process provides a general procedure for preparation of chromene derivatives and is not limited to the preparation of spiropyrans.

This novel process provides a general procedure for the preparation of chromene derivatives, comprising heating a phenol with an appropriate propargyl derivative in a solvent in the presence of a suitable catalyst under mild reaction conditions.

In contrast with reaction conditions normally employed in Claisen rearrangements, the process is carried out at relatively low temperatures, e.g. in boiling xylene or toluene and in the presence of a suitable catalyst. Generally, the reaction temperature should not exceed about 180° C. and is preferably not more than 160° C. or less. The reaction can be expressed in general terms as follows:

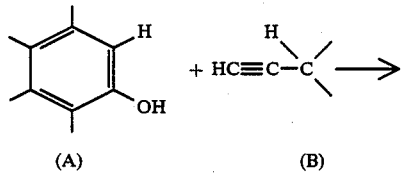
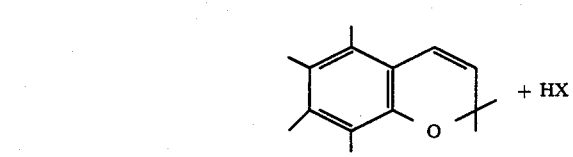

in which (A) can be any phenol and (B) a propargyl alcohol derivative, such as a propargyl acetate. The reaction is catalysted by alumina and proceeds at relatively low temperatures with a marked absence of side reactions. In place of the acetate it is possible to use any aliphatic or aromatic carboxylate, e.g. the propionate or benzoate.

Improved yields are obtained using a propargyl acetate and heating this with a phenol in a solvent such as xylene in the presence of an acidic alumina as catalyst. Surprisingly, these relatively mild conditions bring about a Claisen rearrangement whereas the traditional reaction conditions, e.g. heating to about 210° C. in strongly acid conditions, caused thermal decomposition of the reactants and/or desired product.

The new process provides a convenient one-step synthesis of chromenes using any phenol and the appropriate propargyl acetate or other propargyl alcohol derivative.

Propargyl acetates can be prepared by reacting an appropriate ketone with lithium acetylide. A lithium acetylide/ethylene diamine complex is added with stirring to a solution of the ketone in a suitable solvent, such as tetrahydrofuran or dimethyl sulphoxide. The product is the corresponding propargyl alcohol and the alcohol is conveniently converted to the acetate by reaction with acetyl chloride in a suitable solvent. This process is illustrated in Examples 16 and 17.

The compounds of the present invention and their photochromic properties and procedures for their preparation, is illustrated by the following Examples.

EXAMPLE 1

The reactions and structure of the intermediates and final products for Examples 1, 2, 3, 4, 5.1, 5.3, 5.4, 5.5, and 5.6 are shown below

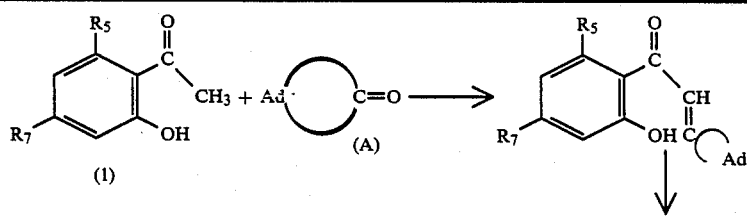

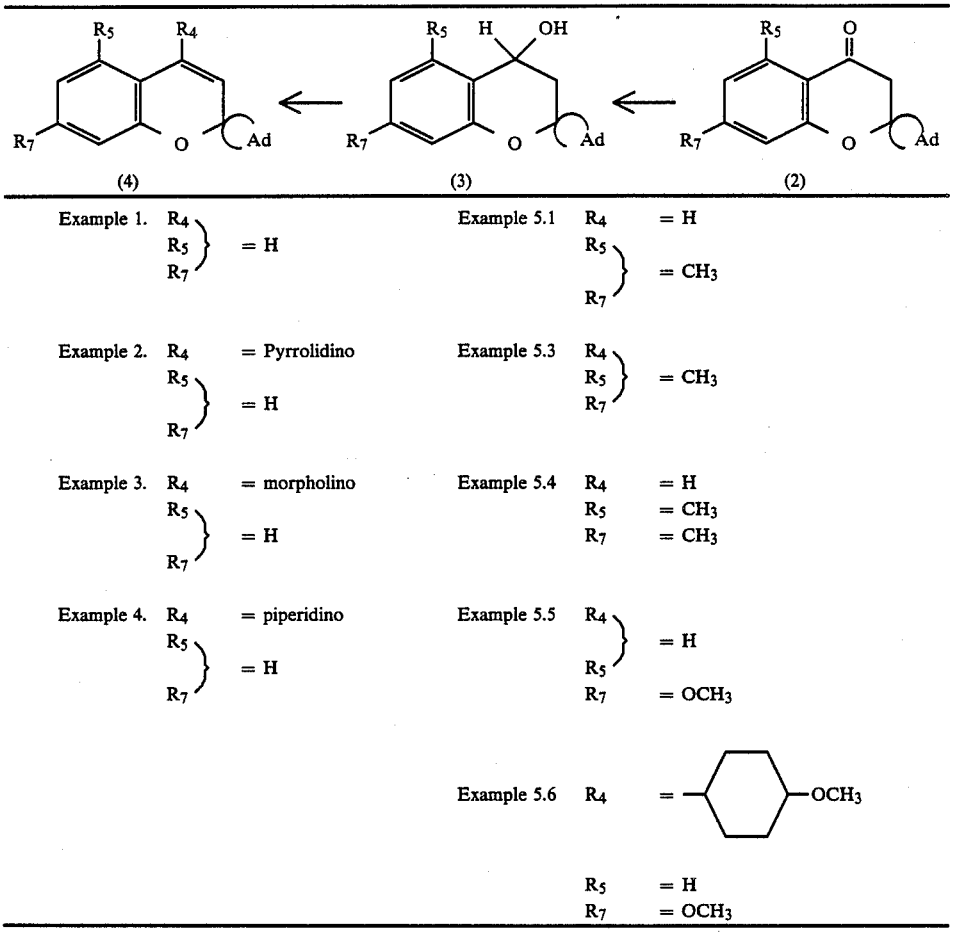

| | | | | | |
|---|---|---|---|---|---|
| Example 1. | $R_4$<br>$R_5$<br>$R_7$ } = H | | Example 5.1 | $R_4$ = H<br>$R_5$<br>$R_7$ } = $CH_3$ | |
| Example 2. | $R_4$ = Pyrrolidino<br>$R_5$<br>$R_7$ } = H | | Example 5.3 | $R_4$<br>$R_5$<br>$R_7$ } = $CH_3$ | |
| Example 3. | $R_4$ = morpholino<br>$R_5$<br>$R_7$ } = H | | Example 5.4 | $R_4$ = H<br>$R_5$ = $CH_3$<br>$R_7$ = $CH_3$ | |
| Example 4. | $R_4$ = piperidino<br>$R_5$<br>$R_7$ } = H | | Example 5.5 | $R_4$<br>$R_5$ } = H<br>$R_7$ = $OCH_3$ | |
| | | | Example 5.6 | $R_4$ = —⟨cyclohexyl⟩—$OCH_3$<br>$R_5$ = H<br>$R_7$ = $OCH_3$ | |

(a) Condensation of adamantanone-with o-hydroxyacetophenone

Adamantanone (100 g) (A) was condensed with ohydroxyacetophenone (1) (100 g) by boiling in toluene (1 dm³) in the presence of pyrrolidine (25 cm³). The water produced was removed as an azeotrope, using a Dean and Stark apparatus. Removal of pyrrolidine and toluene left chromanone (2). (33 g), yellow crystals from acetone.

Reduction of chromanone (2) (15 g) with sodium borohydride (6 g) in methanol (100 cm³) gave, after work up, pure chromanol (3) (12 g), as a colourless oil.

Chromanol (3) (12 g) was dehydrated by heating (5 min) with anhydrous copper sulphate (5 g). The product HC1 (adamantane-2-spiro-2¹[2H-1-benzopyran]—see formula (4), above ($R^4$, $R^5$, $R_7$=H) was extracted with and recrystallised from toluene. The U.V. absorption spectrum of the product, in its colourless state, is shown in FIG. 1 together with spectra of compounds of other Examples.

EXAMPLE 2

The procedure described in Example 1 was repeated using adamantanone (28 g), o-hydroxyacetophenone (30 g) and pyrrolidine (25 cm³) and boiling (5 hours) with removal of water, using a Dean and Stark apparatus. After cooling, the toluene solution was extracted with 5M hydrochloric acid and the aqueous extract was made alkaline using concentrated alkali. The liberated oil was separated and triturated with acetone. The resulting solid was purified by recrystallisation from acetone, giving colourless crystals (22 g). In this Example, the chromanone (formula (2), below reacts with pyrrolidine as shown in the reaction scheme of sheet 6 to give the 4-pyrrolidino-derivative of HCl (compound 5)

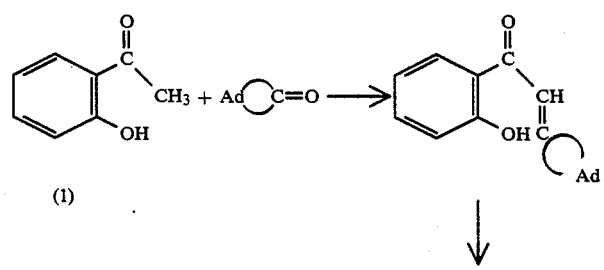

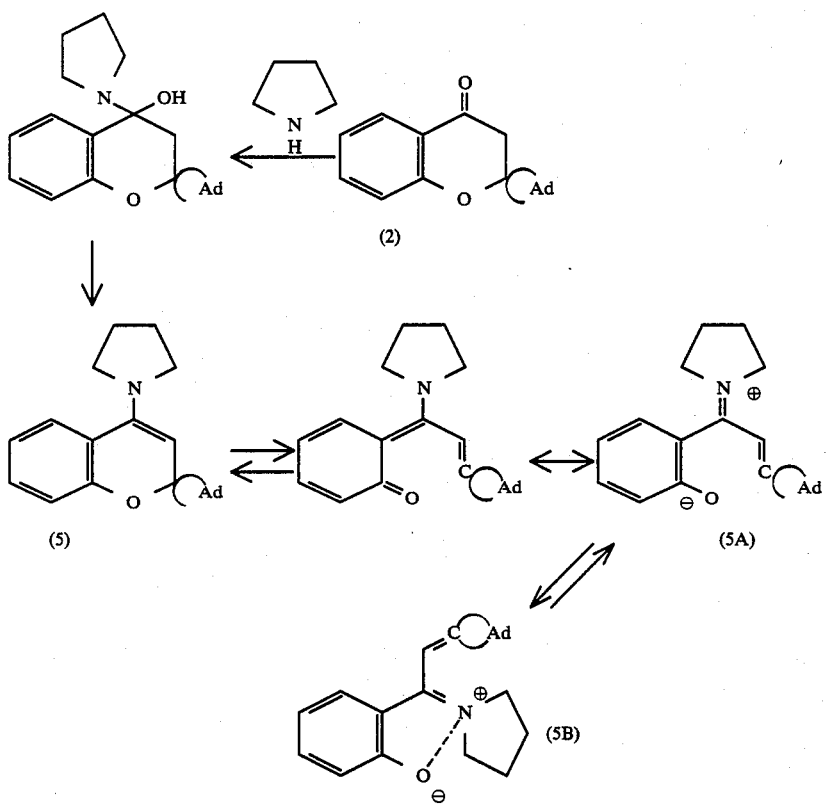

A solution of compound 5 in 1,2-dichloroethane, below 10° C., shows a rapid colourless to orange/yellow colour change in winter sunshine. On irradiation the compound of formula (5) undergoes ring opening to the coloured form, which can exist in the polar states (5A) & (5B). At ambient temperatures, the colour fades rapidly. When compound 5 is dissolved in chloroform (which contains a trace amount of ethanol as stabilizer), the thermal fade occurs much more slowly at ambient temperatures (in the correct order for the sunglass application) and because of this, the solutions show a good response on exposure to a flashgun.

The spectrum of compound 5 in 1,2-dichloroethane shows a strong absorption in the 300–350 nm region which gives rise to the orange/yellow photocolouration.

EXAMPLE 3

Adamantanone (14 g), o-hydroxyacetophenone (15 g) and morpholine (10 cm$^3$) in toluene (200 cm$^3$) and pyrrolidine (0.3 cm$^3$) were boiled (6 hours) and water removed, using a Dean and Stark apparatus. The reaction mixture was worked up as described in Example 2. The product, which was the corresponding 4-morpholino HCl derivative, was obtained as colourless crystals from acetone (6.5 g). The product is less responsive to sunlight than the product of Example 2 under similar conditions.

EXAMPLE 4

Adamantanone (24 g), o-hydroxyacetophenone (15 g) and piperidine (6 cm$^3$) in toluene (200 cm$^3$) were boiled (3 days) and water separated. Work up as described in Example 2 gave (5.5 g) of colourless crystals from acetone. The product, which is the corresponding 4-piperidino HCl derivative, resembles the product of Example 3 in its heliochromic properties.

EXAMPLE 5

Derivatives of the compounds of Examples 2,3 and 4 were prepared by heating adamantanone with a 10% excess of the apropriate o-hydroxyacetophenone and a 50% excess of the cyclic secondary amine in toluene (6–72 hours) with removal of water. Work up was as described in Example 2 and the compound was purified by recrystallisation from acetone.

The 6-methyl derivative of the Example 2 product was prepared starting from 5-methyl-2-hydroxyacetophenone and pyrrolidine. The product was obtained as a colourless oil which shows the same sunlight sensitivity as the Example 2 product and changes to a deep golden yellow on exposure to a flashgun.

The 5,7-dimethyl derivative of the Example 2 product was obtained as colourless crystals, starting from 4,6-dimethyl-2-hydroxyacetophenone and pyrrolidine. It shows a colourless to orange/yellow colour on exposure to a flashgun.

5.1. Preparation of 5$^1$,7$^1$-Dimethyl-adamantane-2-spiro-2$^1$[2H-1-benzopyran]

A mixture of 2,4-dimethyl-6-hydroxyacetophenone (250 g), adamantanone (250 g) and pyrrolidine (125 g) in toluene (1 dm$^3$) was boiled (5 hours) and water separated. Toluene was removed and the residue crystallised from acetone, giving the 5,7-dimethyl-derivative of the enamine of formula (4) under Example 1, (R$^5$, R$^7$=Me and R$^4$=pyrrolidino) (430 g).

Hydrolysis of the enamine (300 g) with conc. hydrochloric acid (25 cm$^3$) in methanol (250 cm$^3$), followed by dilution with water, gave the 5,7-dimethyl chromanone (3) (178 g).

The chromanone (85 g) was reduced with sodium borohydride (30 g) in methanol (1.5 dm$^3$) and the resulting crude chromanol (4) was dehydrated with anhydrous copper sulphate (25 g) to give, 5,7-dimethyl-derivative of HCl as colourless crystals (51 g), from acetone.

5.2 Bromination of 5,7-Dimethyl-HCl

Bromine (2.3 g) was added dropwise to a solution of the compound obtained in Example 5 (5 g) in chloroform (50 cm$^3$). When addition was complete, s-collidine (10 cm$^3$) was added and the reaction mixture boiled (6 hours). Work up gave an oil containing a mixture of products, from which the 6,8-dibromo-5,7-dimethyl-derivative of HCl was isolated as colourless crystals.

5.3. 4,5,7-Trimethyl derivative of HCl

An excess of methylmagnesium bromide in ether was added to 5,7-dimethyl-chromanone (2) (see Example 1, R$^5$, R$^7$=CH$_3$) (3 g), the reaction mixture boiled (1 hour) and poured into dilute hydrochloric acid. Work up gave an oil which was boiled in toluene containing a few crystals of p-toluenesulphonic acid and water was removed. The 4,5,7-trimethyl-derivative of the compound of Example 1 was obtained as colourless crystals.

5.4. Heliochromic Response of 5,7-Dimethyl-derivatives of HCl

The 5,7-dimethyl derivative shows a colourless to orange colour change on filter paper or in 1,2-dichloroethane at low temperatures. The 6,8-dibromo-5,7-dimethyl-derivative shows a colourless to red colour change under similar conditions. The 4,5,7-trimethyl and 4-phenyl-5,7-dimethyl derivatives show such a marked increase in the thermal fade of their coloured forms that no heliochromic response can be detected for chloroform solutions, even at −60° C.

5.5. The Synthesis of 7-Methoxy Derivatives of HCl

Because of its electron releasing properties, the introduction of a 7-methoxy group into the compound of Example 1 might be expected to give rise to a coloured form with enhanced dipolar character compared to the compound of Example 1, which would influence the absorption characteristics and the thermal fade rate of the coloured form as illustrated below:

Preparation of 7 Methoxy-HCl

A mixture of 2-hydroxy-4-methoxyacetophenone (10 g), adamantanone (9 g), pyrrolidine (5 cm$^3$) in toluene was boiled (10 hours) and water was separated. Solvent was removed and the residue crystallised from acetone to give the corresponding chromanone (6 g).

The 7-methoxychromanone (2.8 g) in methanol was reduced with sodium borohydride. The reaction mixture was boiled (1½ hour), methanol removed and the residue dissolved in ether and washed with water. Work up gave the chromanol (1.1 g), which gave colourless crystals from petroleum, (b.p. 60°–80° C.).

Crude 7-methoxychromanol (4 g) was heated with anhydrous copper sulphate (1.3 g) in a test tube over a bunsen flame for several minutes. The product was cooled and extracted with hot petroleum, from which the 7-Methoxy-HCl compound (1.2 g) crystallised.

In dichloroethane, the 7-methoxy-derivative showed a colourless to yellow heliochromic response on exposure to a flash gun and an acceptable thermal fade at ambient temperatures.

5.6. Preparation of 4-p-Anisyl-7-methoxy-derivative of HCl 7-methoxychromanone (2.3 g) (Example 5.5) in tetrahydrofuran was added to a solution of p-anisylmagnesium bromide [from p-bromoanisole (18.7 g) and magnesium (2.4 g) in tetrahydrofuran (100 cm$^3$)]. The reaction mixture was boiled (1 hour), part of the solvent removed, and the residual oil poured into dilute hydrochloric acid. Work up gave the 4-p-anisyl-7-methoxy-derivative of the Example 1 compound, (1.9 g), as colourless crystals from ethanol.

The thermal fade of the coloured form of this compound is so rapid (attributed to steric effects of the bulky 4-p-anisyl group) that the colourless to orange colour change on exposure to a flash gun can be seen only with difficulty on cooled impregnated filter paper.

5.7. Synthesis of 6-Methyl-derivative of HCl

A mixture of 2-hydroxy-5-methylacetophenone (5 g), adamantanone (5 g) and pyrrolidine (3 g) in toluene (100 cm$^3$) was boiled (17 hours) until all the water had separated. Toluene was removed, leaving the 6-methyl-derivative of the Example 2 compound as an oil which could not be induced to crystallise. It was hydrolysed by boiling with conc. hydrochloric acid (3 cm$^3$) in methanol (100 cm$^3$) to the chromanone. Reduction of the latter with sodium borohydride in methanol gave the chromanol in near quantitative yield. Dehydration of the chromanol with anhydrous copper sulphate gave 6-methyl-derivative of the Example 1 compound as colourless crystals after recrystallisation from acetone.

5.8. Synthesis of 6,7-Dimethyl derivative of HCl

A mixture of 2-hydroxy-4,5-dimethylacetophenone (10 g), adamantanone (10 g) and pyrrolidine (5 g) in toluene (75 cm$^3$) was boiled (10 hours) and water separated. Removal of solvent left the 6,7-dimethyl-derivative of the Example 2 compound as an orange oil which could not be induced to crystallise. It was hydrolysed with conc. hydrochloric acid (0.5 cm$^3$) in methanol (50 cm$^3$) to the chromanone. Reduction of the latter with sodium borohydride (2.5 g) in methanol gave the chromanol which was dehydrated by heating with anhydrous copper sulphate (2 g) to give the 6,7-dimethyl derivative of the Example 1 compound (3.1 g), pale yellow crystals from ethanol.

The 6-Methyl- and 6,7-dimethyl derivatives of the Example 1 compound in chloroform or dichloroethane at ambient temperatures, change from colourless to orange on exposure to a flash gun, with a thermal fade rate at ambient temperature suitable for the sunglass application. Their behaviour in this respect is superior to that of the product of Example 1.

5.9 Synthesis of 6-Phenyl-derivatives of HCl

A mixture of p-phenylphenol (85 g), acetic anhydride (200 cm$^3$) and conc. sulphuric acid (10 drops) was boiled (1½ hours), cooled and poured into water. The acetate was filtered off and recrystallised from ethanol, giving colourless crystals in near quantitative yield.

The acetate (42 g) in tetrachloroethane (100 cm$^3$) was added to anhydrous aluminium chloride (30 g) in tetrachloroethane (100 cm$^3$) and heated (2 hours) at 140° C.

with stirring. The rection mixture was cooled and poured into hydrochloric acid and crushed ice. Work up gave 5-phenyl-2-hydroxy-acetophenone (35 g).

A mixture of 5-phenyl-2-hydroxyacetophenone (35 g), adamantanone (25 g) and pyrrolidine (17 cm$^3$) in toluene (250 cm$^3$) was boiled (3 hours) and water separated. Toluene was removed and the residual 6-phenyl-derivative of the product of Example 2 boiled (20 minutes) with methanol (200 cm$^3$) containing conc.hydrochloric acid (2 cm$^3$). Work up gave the chromanone (18.5 g). The chromanone (12.5 g) was reduced with sodium borohydride (4 g) in methanol (150 cm$^3$). Work up gave the chromanol (8 g), as colourless crystals from dichloromethane and light petroleum. The chromanol was dehydrated by heating (10 minutes) with anhydrous copper sulphate (1.5 g). The 6-phenyl derivative of the Example 1 compound was extracted with dichloromethane and recrystallised from acetone, pale yellow crystals, m.p. 114°–115° C., (3.8 g).

The 6-phenyl-derivative impregnated into paper or dissolved in dichloroethane changed from colourless to purple on exposure to a flash gun with a thermal fade at ambient temperatures.

5.10. Synthesis of the 8-propyl HCl derivative (5)

3-Acetyl-5-propyl-5,6,7,8-tetrahydro-2-naphthol (1) was reacted with adamantanone and pyrrolidine in toluene to give the corresponding derivative of the Example 2 compound (2) which was hydrolysed, with methanol containing a few drops of conc. hydrochloric acid, to the chromanone (3). Reduction of the chromanone (3) (2.7 g) with sodium borohydride (0.7 g) in methanol, gave the chromanol (4) (2.7 g), which was dehyrated by heating with anhydrous copper sulphate (1 g) to yield the product (5) colourless crystals from methanol (1.8 g).

When exposed to a flashgun, the product impregnated into filter paper or dissolved in dichloroethane, showed a colourless to orange-red colour change with an acceptable thermal fade rate at ambient temperatures. Compared to the 6-methyl- and 7-methoxy-derivatives of HCl, its photochromic response was weaker.

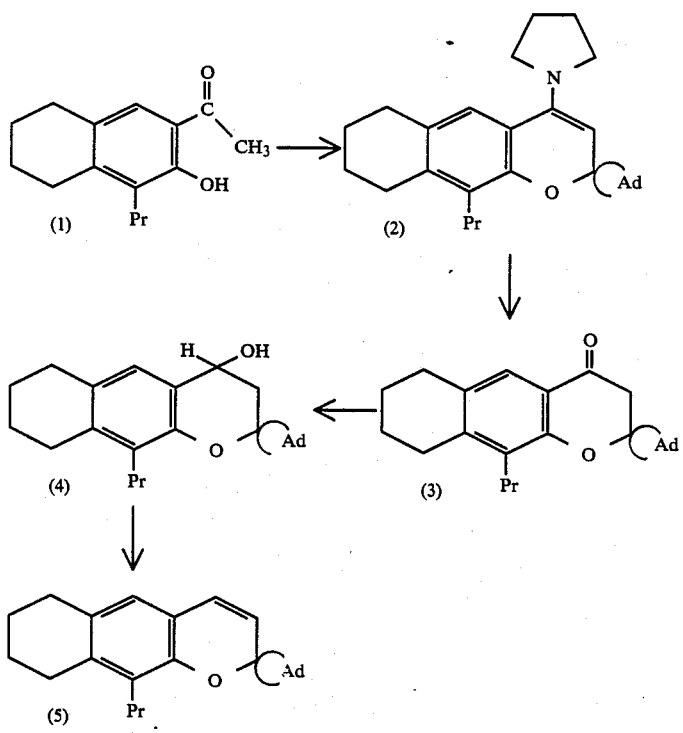

Pr = CH$_3$.CH$_2$.CH$_2$—

EXAMPLE 6
Synthesis of compounds of HC7 series

SCHEME 1

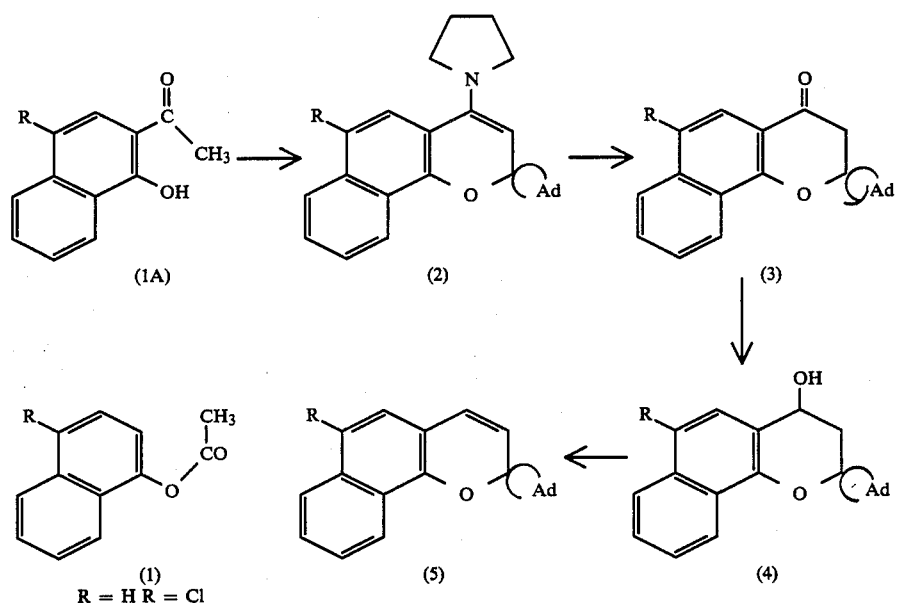

(1)
R = H R = Cl

A mixture of 1-hydroxy-2-acetonaphthone (10.1 g), (1A), adamantanone (9 g) and pyrrolidine (10 cm³) in toluene (300 cm³) was boiled (10 hours) and water separated. The yellow reaction mixture turned first crimson and then dark brown. Toluene was removed under reduced pressure and the residual enamine crystallised from acetone as discoloured crystals (8 g). The enamine (2) (10 g) was treated with conc. hydrochloric acid (1 cm³) in methanol (200 cm³). The crimson solution was evaporated and the residual dark oil crystallised from acetone, yielding the chromanone (3) (8.4 g) as yellow needles. The chromanone (0.5 g) was reduced by sodium borohydride (0.5 g) in methanol to yield the chromanol (4) (0.32 g) which was heated with anhydrous copper sulphate to give HC7 (formula (5) R=H) (0.28 g) as a discoloured solid which was decolourised with activated charcoal and recrystallised from acetone.

Solutions of the product in chloroform of dichloroethane show a colourless to intense orange colour change on exposure to a flashgun, which fades to yellow at ambient temperatures. On warming the solutions, the yellow colour fades completely.

Figure 2:
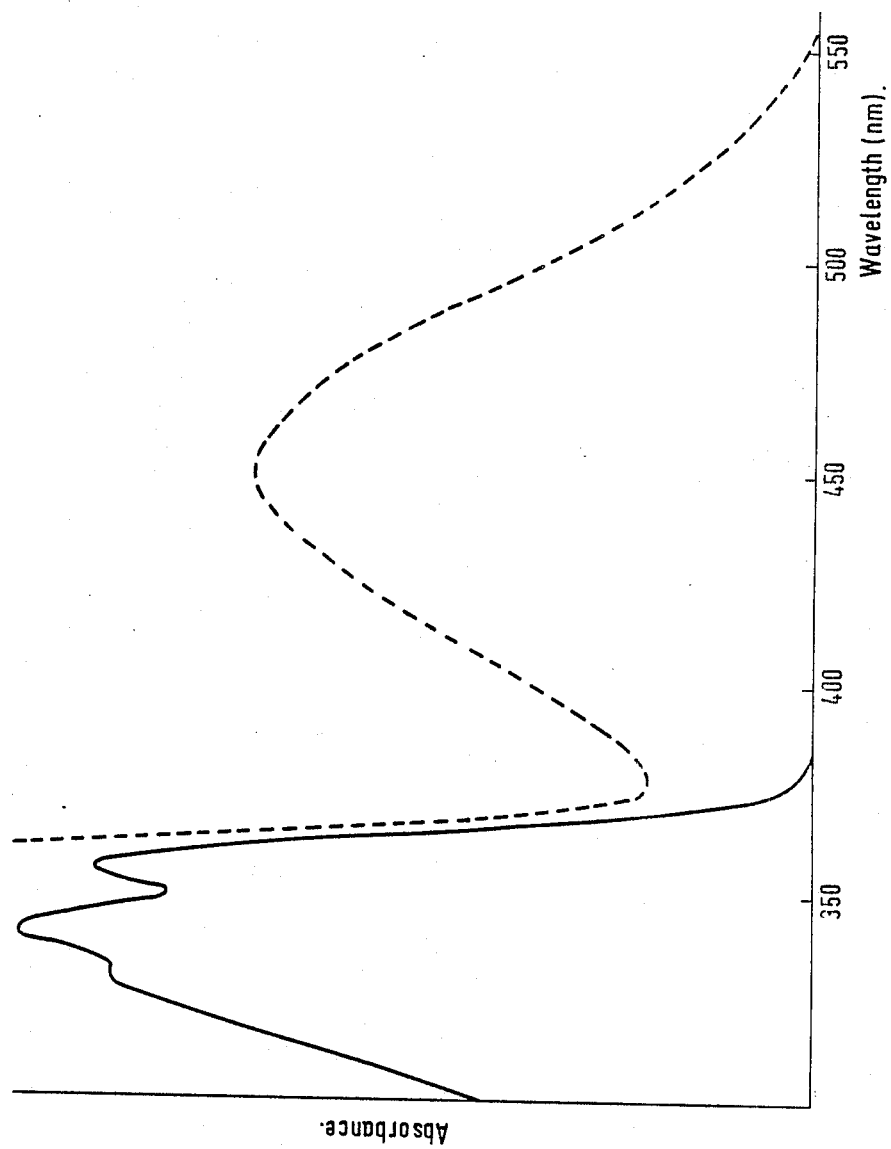
FIG. 2 shows the ultra violet and visible spectra of the compound of Example 6 before and after exposure to a photographic flashgun.

The spectrum of the product in dichloromethane shows the required shift of the absorption band in the ultraviolet region (see FIG. 1). The spectrum of the product of this Example before and after exposure to a flashgun is shown in FIG. 2.

EXAMPLE 7
4-Phenyl derivative of HC7

Phenyl lithium in cyclohexane and ether (10 cm³ of a 2.47 molar solution) was added to the chromanone of Example 6 (1.8 g) in tetrahydrofuran (50 cm³) under nitrogen. The mixture was stirred (½ hour) and poured onto ice. The organic solvents were removed and the aqueous layer acidified with hydrochloric acid and extracted with toluene. Work up gave the 4-phenyl-derivative of the HC7 (

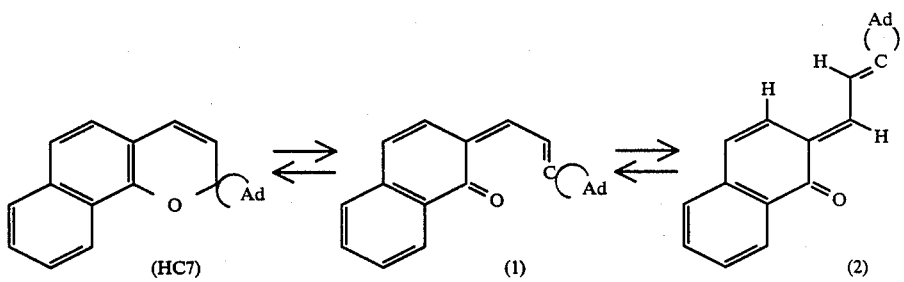

formula (V), $R^6$=H $R_4$=$C_6H_5$ (2 g), a colourless crystalline powder after crystallisation from acetone. The 4-phenyl-derivative was not heliochromic at ambient temperatures but in chloroform at −60° C., the solution turned orange-red, on exposure to a flash gun. Its UV absorption spectrum is shown in FIG. 1.

EXAMPLE 8 (see sheet 5) Preparation of HC57

8.1 Preparation of 2-Adamantylideneethan-1-ol (8)

Ethyl adamantylideneacetate (7) (31 g) in tetrahydrofuran (50 cm³) was added dropwise to a suspension of lithium aluminium hydride (5.2 g) in tetrahydrofuran (30 cm³). When the addition was complete, the reaction 0° C., allowed to warm up to room temperature and poured onto crushed ice. Work up gave the alcohol (8) (8.8 g) as a colourless oil which partially crystallised.

8.2 Preparation of 2-Adamantylidene-1-ethyl Bromide (9)

Phosphorus tribromide (8.5 g) was added slowly to a stirred solution of adamantylidene ethanol (8) (18.8 g) in ether (250 cm³) at 0° C.. The mixture was stirred for 1 hour and then carefully poured into water. Work up gave adamantylidene ethyl bromide (9) (19.3 g) as a yellow oil.

8.3 Preparation of 2-Adamantylidene 1 ethyltriphenylphosphonium Bromide (10)

Triphenylphosphine (19.1 g) was added to adamantylidene ethyl bromide (9) (19 g) dissolved in dry ether. The mixture was boiled (3 h) and the phosphonium salt (10) (26 g) was filtered off.

8.4 Preparation of the Spiropyran (HC57)

Figure 3:
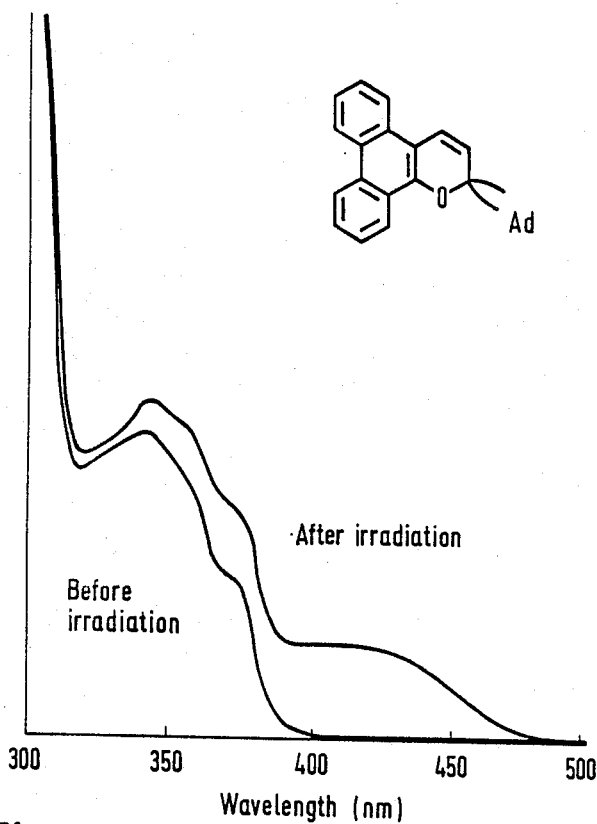
FIG. 3 shows the spectra of the compound of Example 8 before and after exposure to a photographic flashgun.

A mixture of the phosphonium salt (10) (2 g) and sodium methoxide (2 g) in dry ether was stirred under nitrogen for 1 hour. The solution turned red due to the formation of the phosphorane (11). Phenanthroquinone (0.5 g) dissolved in dry ether (100 cm³ was added and the solution was boiled (2 h) and left to stir at room temperature overnight. The solution was filtered and the filtrate evaporated. The residue was chromatographed on silica gel and the photochromic compound of formula 12 was recrystallised from ethyl acetate. Its heliochromic response is to yellow and its qualitative spectrum in chloroform before and after exposure to a flashgun, is shown in FIG. 3.

EXAMPLE 9

9.1 Acetylation

2-Naphthol (1) (70 g) in glaiial acetic acid (40 cm³) was treated with redistilled boron trifluoride etherate (200 cm³) and the mixture was boiled (2 h). On cooling, 1-acetyl-2-naphthol (2) (62 g) crystallised out.

9.2 Condensation, Reduction and Dehydration

A mixture of 1-acetyl-2-naphthol (2) (35 g) adamantanone (25 g) and pyrrolidine (40 cm³) in toluene was boiled (12 h) using a Dean and Stark apparatus. The solution turned first crimson and then brown. When all the water had been removed, toluene was distilled off under reduced pressure and the residual dark brown oil gave solid chromanone (3) (35 g) after trituration with acetone. Chromanone (3) (6 g) in tetrahydrofuran (100 cm³) was reduced with lithium aluminium hydride (1 g) suspended in tetrahydrofuran (20 cm³). The reducing agent was added dropwise at the rate required to maintain gentle reflux in this exothermic reaction. When the addition was complete, the mixture was boiled (10 minutes) and stirred (3 h). Ethyl acetate was added to react with the excess lithium aluminium hydride. Solvent was removed and water was added to the residue. The organic material was extracted into chloroform. The chloroform extract was dried over anhydrous magnesium sulphate and filtered. Removal of solvent left chromanol (4,R=H) (4.5 g).

Chromanol (4,R=H) (4.5 g) was melted and treated with freshly prepared anhydrous copper sulphate (0.5 g) and the mixture was heated gently over a bunsen flame for 10 minutes. The mixture was cooled and extracted with chloroform. The chloroform extract, on evaporation, left chromene (5,R=H), (HC5), which crystallised from acetone in tan coloured needles (2.5 g).

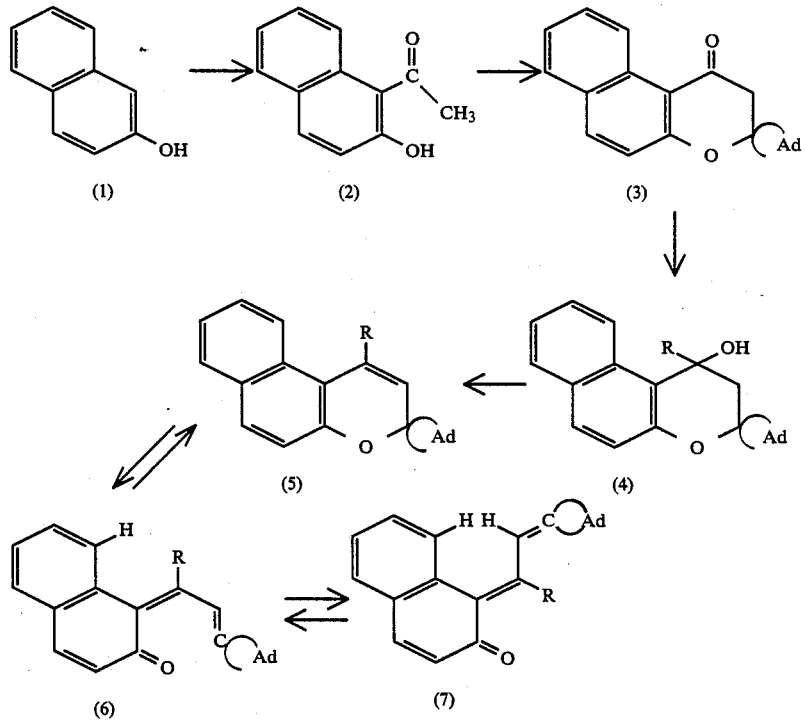

Preparation of HC5 Compounds

Characterisation of HC5 Chromene

The HC5 chromene shows a heliochromic response from colourless to yellow and a much faster thermal fade than the compound of Example 6 at ambient temperatures. The coloured form can exist in the cis and trans configurations (6) and (7).

EXAMPLE 10

Preparation 4-methyl- Derivative of HC5

Chromanone (3)(see Example 9)(2 g) in ether (100 cm$^3$) was treated, under nitrogen, with methyl-lithium (1.5 molar solution in ether, as a complex with lithium bromide (20 cm$^3$) and boiled (4 h). The mixture was poured onto ice and carefully acidified. Work up gave the chromene (5,R=Me)(see Example 9)(0.5 g). A solution 4-methyl-HC5 (5,R=Me) in chloroform at liquid nitrogen temperatures is heliochromic, showing a colourless to yellow colour change with a rapid fade at this temperature. The lack of photochromic properties at ambient temperatures is attributed to an extremely fast thermal fade.

EXAMPLE 11

Preparation of 4-Phenyl HC5 Derivative

Chromanone (3) (See Example 9) (1.5 g) in tetrahydrofuran (20 cm$^3$) was treated with phenyl-lithium (2.7 molar solution in diethylether/cyclohexane) (20 cm$^3$) under nitrogen The mixture was stirred (½ h) and poured onto crushed ice. Work up gave an oil which crystallised from acetone to give 4-phenyl-HC5 (5,R=Ph) (See Example 9) as fine crystals (1.5 g).

Like 4-methyl-HC5 (5, R=Me), 4-phenyl-HC5 (5, R=Me) is not photochromic at ambient temperatures, presumably because of the fast thermal fade of the coloured form. At liquid nitrogen temperatures, 4-phenyl-HC5 in chloroform, like 4-methyl-HC5 in chloroform, shows a colourless to yellow colour change. The yellow colour fades rapidly.

Characterisation of 4-Methyl and 4-Phenyl-HC5

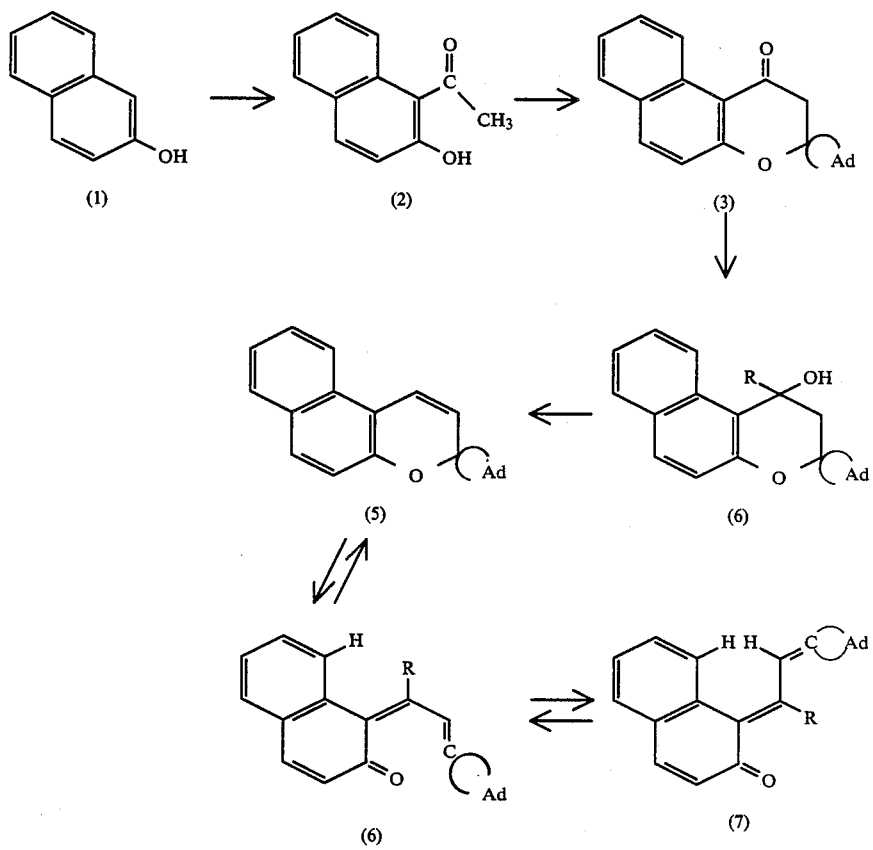

The interactions of the 4-substituent (methyl or phenyl) with the carbonyl group destabilises the yellow transoid form (Structure 7, R=Me or Ph), which isomerises to the less sterically hindered yellow cisoid form (Structure 6, R=Me or Ph), which, in turn shows a fast thermal ring-closure to HC5 (Structure 5, R=Me or Ph).

EXAMPLE 12

12.1 Preparation of 4-p-Methoxyphenylphenol (2)

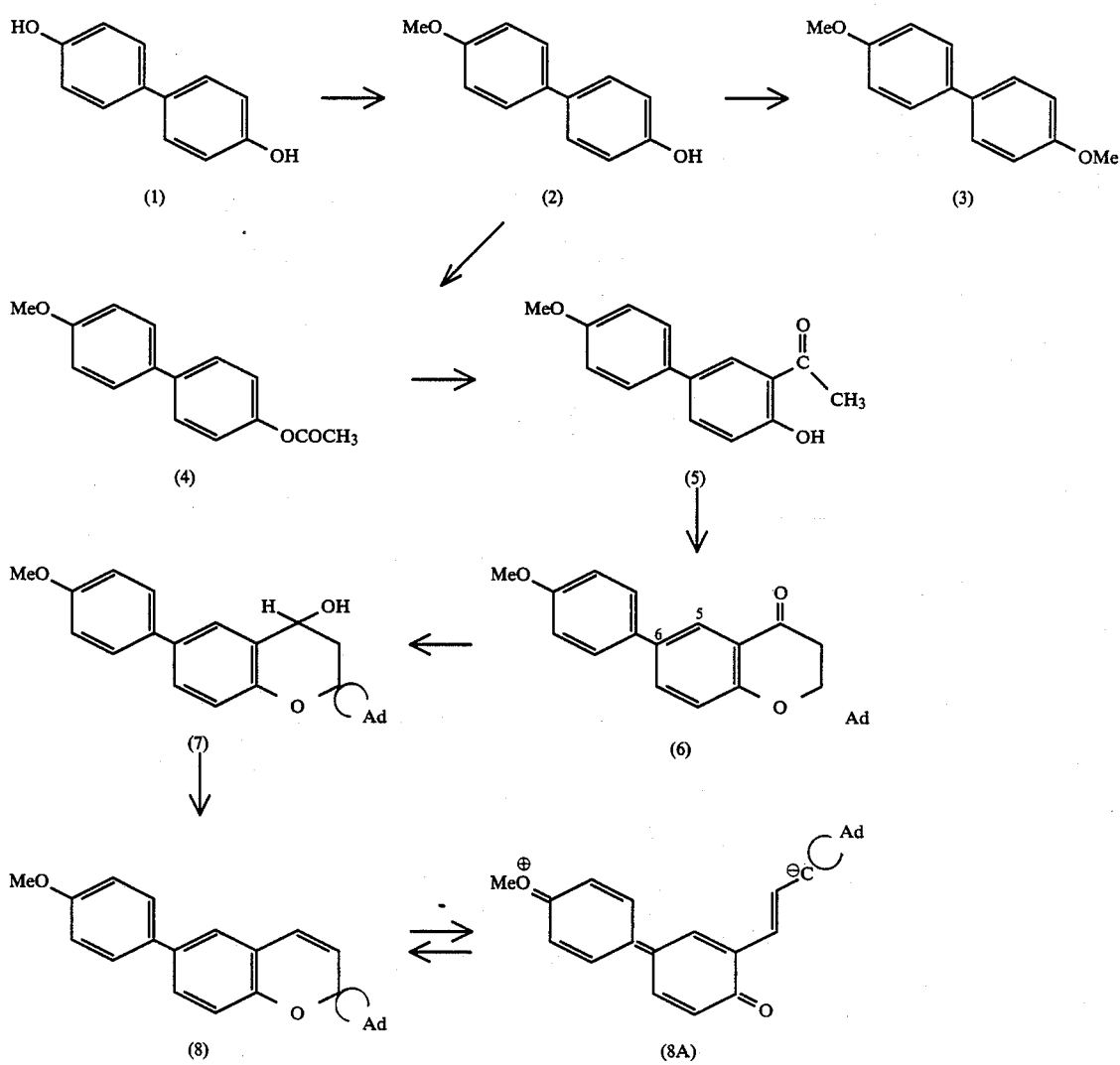

The procedure was as follows:

4,4'-Dihydroxydiphenyl (1) (32 g 0.17 mol) was dissolved in 2M solution hydroxide solution (0.34 mol) and dimethyl sulphate (22 g 0.175 mol) was added slowly with stirring over half an hour. The sodium salt of the required product was filtered off and dried. The yield was 24 g. The sodium salt of the phenol (24 g) was treated with acetyl chloride (150 cm$^3$), filtered and excess acetyl chloride removed. Work up gave 4- methoxy-4'-acetoxydiphenyl (4) (22 g).

12.2 Preparation of 2-Acetyl 4-p-Methoxyphenylphenol (5)

4-Methoxy-4'-acetoxydiphenyl (4) (7 g) was subjected to a Fries rearrangement by heating with anhydrous aluminium chloride (5 g) in tetrachloroethane (50 cm$^3$) at 140° C. Hydrogen chloride was evolved and the green reaction mixture changed to orange and became viscous. After half an hour, the reaction mixture was cooled and 5M hydrochloric acid was added. The organic layer was extracted with chloroform, washed with water, dried (MgSO$_4$) and filtered. Solvent was removed from the filtrate. N.m.r. studies showed that the residual yellow oil was a ca. 1:1 mixture of the required product (5) and a second component.

12.3 Preparation of 6-p-Methoxyphenyl-HCl

The 1:1 mixture, obtained above (5 g) adamantanone (3 g), pyrrolidine (2.5 cm$^3$) and toluene (100 cm$^3$) were mixed and boiled (4 h). A red lower layer was formed which is not observed as a rule for these reactions when pure reactants are used. The upper toluene layer was decanted off and solvent was removed. The residue was boiled with conc.hydrochloric acid and methanol to hydrolyse any enamine to the chromanone (6).

Methanol was removed and the acidic mixture was extracted with ether. Pure chromanone (6) (0.5 g) was obtained from the dried ether extract on concentration and has been retained. The chromanone (6) was reduced with sodium borohydride in methanol to the chromanol (7), which was dehydrated by heating with freshly prepared anhydrous copper sulphate. 6-p-Methoxyphenyl-HCl (8) was extracted from the copper sulphate with chloroform. The chloroform solution was impregnated on filter paper. The paper showed a heliochromic response to purple on exposure to a flash gun. The coloured polar form is shown in structure (8A).

The fade was slower than for other HCl derivatives apart from 6-methoxy HCl.
EXAMPLE 13
6-p-Methoxyphenyl-HC7
(a) The preparation of 4,4-bis-p-methoxyphenyl-but-3-enoic acid (5)
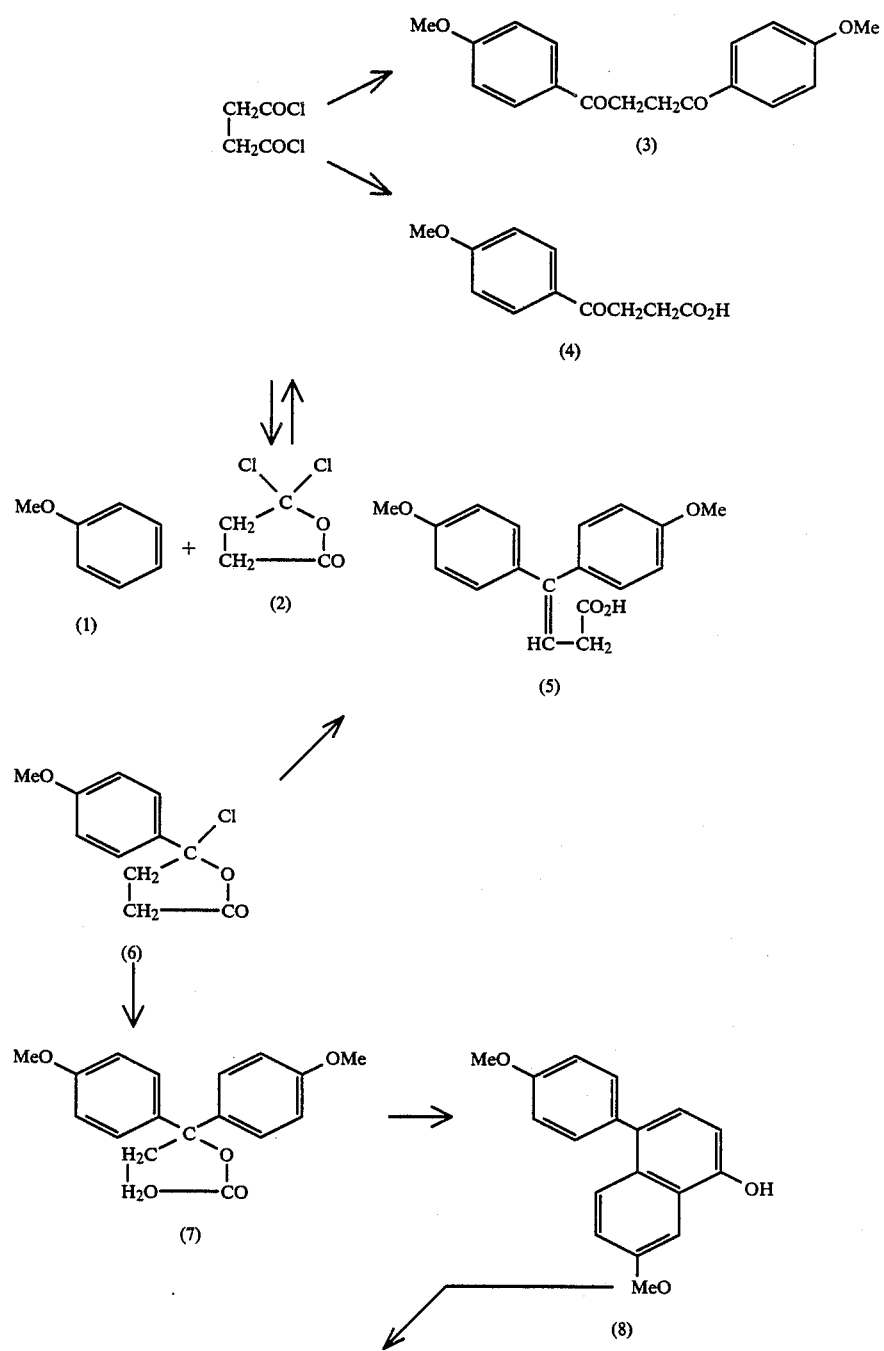

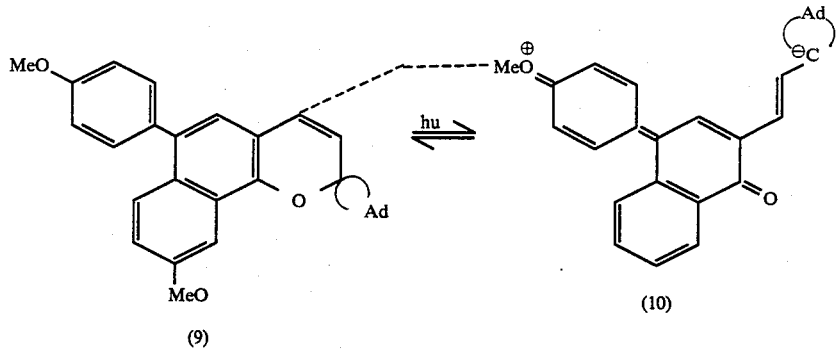

(a) A mixture of anisole (1) (46.6 g) and succinyl dichloride (2) (35 g) in 1,2-dichloroethane (100 cm³) was added dropwise over ½ h to anhydrous aluminium chloride (41.6 g) in 1,2-dichloroethane (100 cm³) maintained at 0° C. The mixture was left overnight at room temperature, diluted with chloroform poured into water, washed with water, and carefully extracted with 10% sodium carbonate solution.

(b) The sodium carbonate solution (referred to above) was acidified to give the acid (5) (20 g) which was boiled with acetic anhydride (100 cm³) and sodium acetate (5 g) to give 4-p-methoxyphenyl-7-methoxy-1-naphthyl acetate (18 g) which was hydrolysed to the naphthol (8) (13.2 g).

Figure 4:
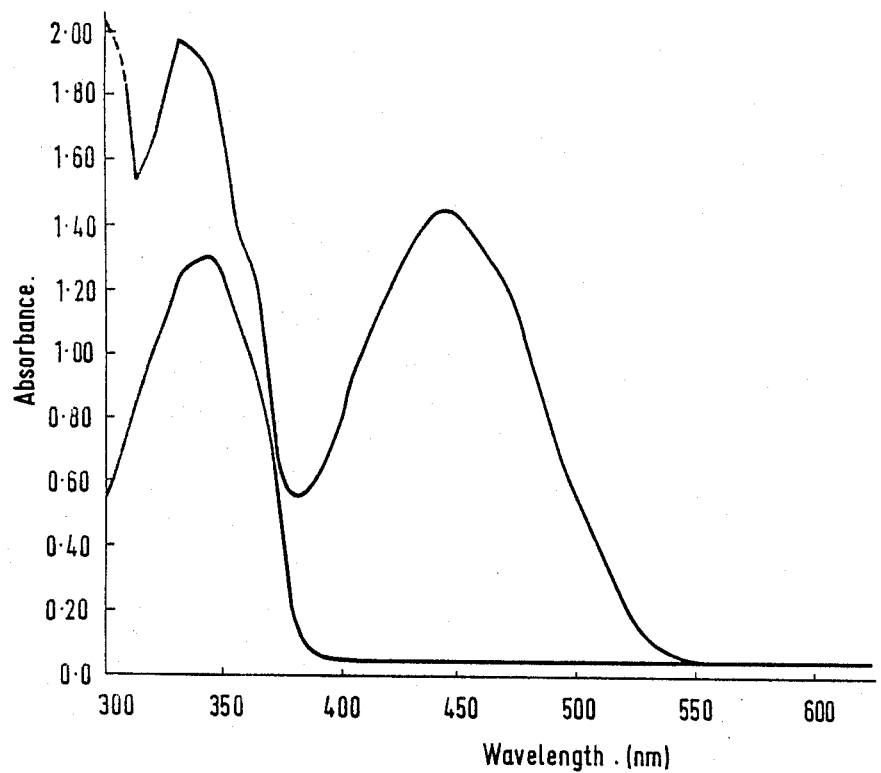
FIG. 4 shows the spectra of the compound of Example 13 before and ater exposure to light from a flash gun.

A mixture of the naphth ol (8) (10.3 g), adamantylideneacetic acid (7.1 g) and boron trifluoride etherate (100 cm³) was boiled for 10 min. Deep red crystals of product (12.3 g) separated and were filtered off. This product (2.7 g) in 1-butanol was reduced with sodium borohydride, giving 6-p-methoxyphenyl-9-methoxy-HC7 (9) (0.6 g) as near colourless crystals from ethanol, m.p. 208°–209° C. Its solutions show a heliochromic response to red i.e. a much deeper colour than obtained from 6-phenyl-HC7, demonstrating the important and marked effect of the p-methoxy substituent. The spectra is shown in FIG. 4.

EXAMPLE 14

Preparation of 6-chloro-HC7

(a) Acetylation and Fries Rearrangement

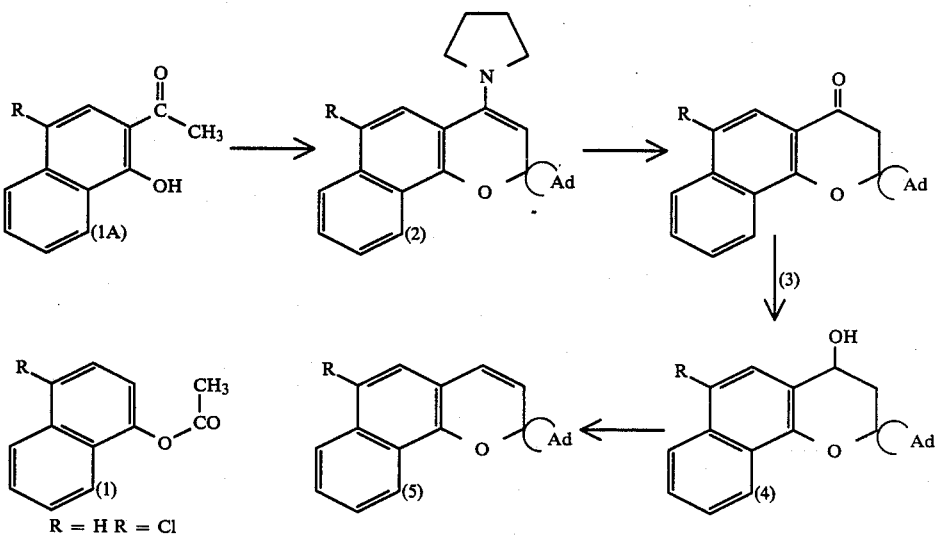

4-Chloro-1-naphthol (50 g) was boiled with acetic anhydride (200 cm³) containing a few drops of conc.sulphuric acid for 1½ hours. The resulting ester (1) (R=Cl) was obtained as an oil which was dissolved in tetrachloroethane (150 cm³) to which anhydrous aluminium chloride (33 g) was added. When the copious evolution of hydrogen chloride had subsided, the mixture was heated (1½ h) at 130° C. The dark viscous mixture was poured into ice and hydrochloric acid and extracted with chloroform. The chloroform extract was dried (anhydrous magnesium sulphate) filtered and evaporated, leaving 2-acetyl-4-chloro-1-naphthol (28 g).

(b) Condensation, Reduction and Dehydration

A mixture of 2-acetyl-4-chloro-1-naphthol (1) (28 g), adamaqntanone (20 g) and pyrrolidene (20 cm³) in toluene (250 cm³) was boiled for 3 hours and water was removed. Work up, as for HC7, gave 6-chlorochromanone (3) (29 g) as dark green discoloured crystals. the n.m.r. spectrum indicated that the product is the chromanone (3) except for the highly coloured dark green impurity.

6-Chlorochromanone (3) (20 g) was reduced with sodium borohydride (11 g) in 1-butanol (300 cm³). 6-Chlorochromanol (4) (11.9 g) was obtained as a dirty white powder.

6-Chlorochromanol (4) (5.5 g) was heated with anhydrous copper sulphate, as previossly described, to give the chromene (5), 6-chloro-HC7, decolourised by heating with charcoal in ethyl acetate. It crystallised from the same solvent as off-white crystals (6 g).

Characteristics of 6-Chloro-HC7

Figure 5:
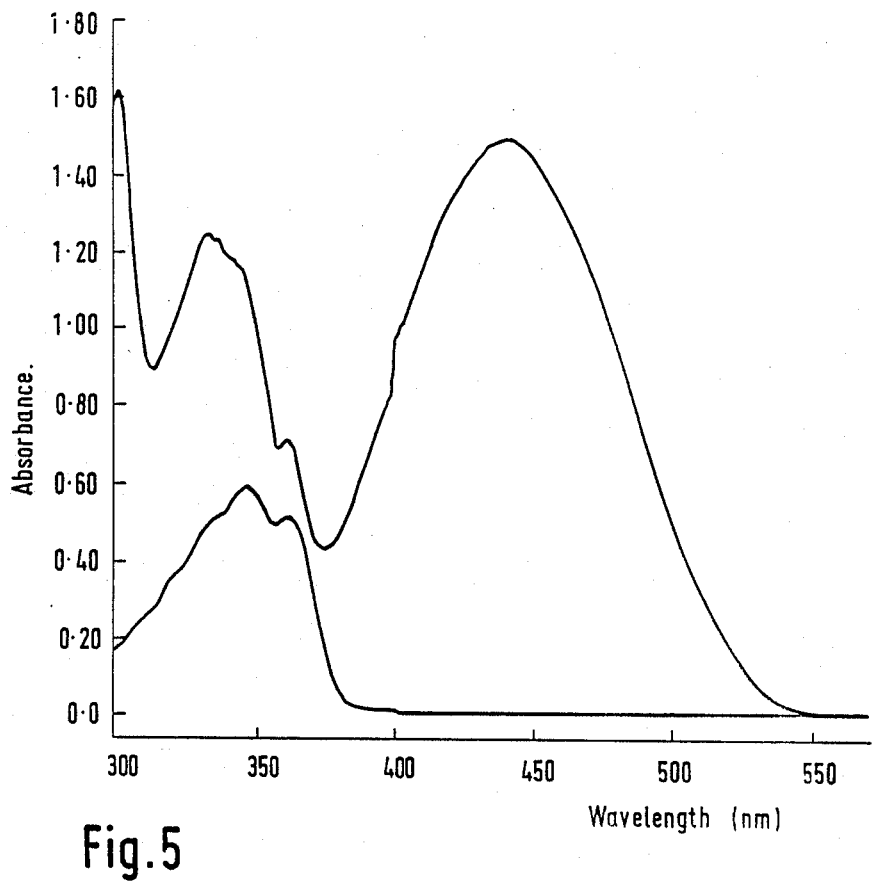
FIG. 5 shows the spectra of the compound of Example 14 before and after exposure to a flash gun.

The ultraviolet spectrum of 6-chloro-HC7 in toluene is similar to the spectrum of HC7 in toluene and is shown in FIG. 5. The spectra of their coloured forms are also similar, but on irradiation under the same conditions, there is a much larger conversion of 6-chloro-HC7 into its coloured form than is obtained for HC7 and the sensitivity to colouring of 6-chloro-HC7 is higher than for HC7. Their thermal fade rates are similar. The absorption band of the uncoloured form is shifted to longer wavelengths compared with HC7 to give, on irradiation, a coloured form having a high molar extinction coefficient. Thermal reverse and its alteration in toluene under irradiation is similar to HC7. The sensitivity to sunlight is significantly higher than the parent compound. This is summarised below:

|      | Cod | AM-2 Response | | |
|------|-----|---|---|---|
|      |     | OD at 8 sec. | at 60 sec. | at saturation |
| HC7  | $1.66 \times 10^{-4}$ | 0.25 | 0.59 | 0.84 |

-continued

|      | Cod | AM-2 Response | | |
|------|-----|---|---|---|
|      |     | OD at 8 sec. | at 60 sec. | at saturation |
| 6-Cl-HC7 | $1.76 \times 10^{-4}$ | 0.4 | 0.87 | 1.2 |

Cod = Conc. × thickness of sample in cast film of cellulose acetate.
OD = Optical density
AM-2 is a standard light source having a spectral output similar to sunlight.

EXAMPLE 15

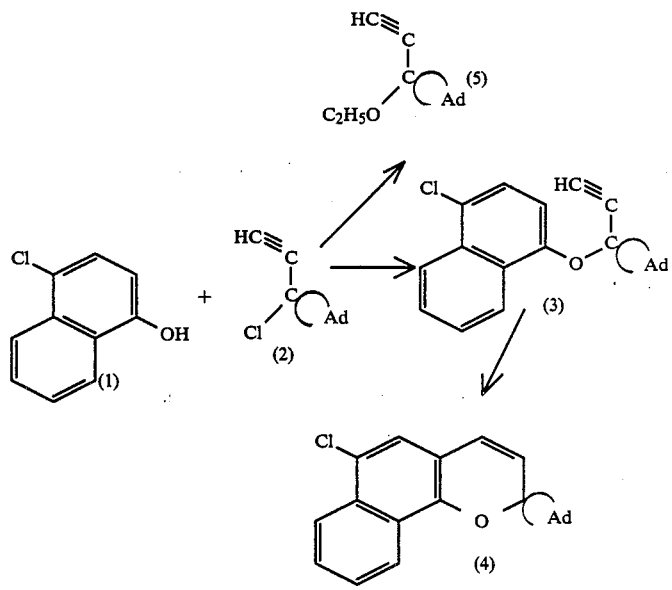

This Example illustrates the preparation of 6-chloro-HC7 by a Claisen rearrangement type reaction in the presence of alkali.

4-Chloro-1-naphthol (1) (17.8 g, 0.1 mol) was dissolved in a solution of potassium hydroxide (6.2 g, 0.1 mol) in 1:1 water/ethanol (200 cm³) and ethynyladamantyl chloride (2) (19.4 g, 0.1 mol) was added slowly with stirring. The mixture was stirred (4 hours) and ether was added (100 cm³). The ether layer was separated, washed with dilute KOH solution and then with water. The ether layer was dried using magnesium sulphate and filtered.

The product contained the 6-chloro-HC7 (4), together with the propargyl ether (3) and a large amount of the ether (5).

The ethynyl-adamantanyl chloride was prepared as follows

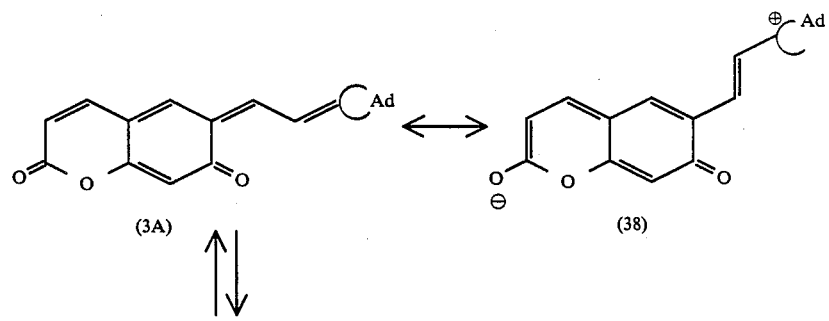

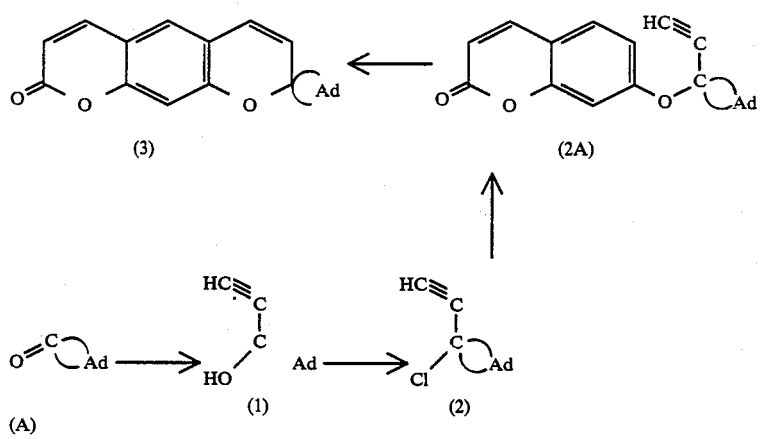

(A)

Lithium acetylide, complexed with ethylenediamine (50 g) was added slowly to adamantanone (A) (82 g) dissolved in dry tetrahydrofuran (200 cm³). When the exothermic reaction was complete, the mixture was stirred (3 h) at room temperature, poured onto crushed ice and acidified with dilute hydrochloric acid. Work up gave the alcohol (1) which was treated with thionyl chloride (200 cm³), added gradually with shaking and the reaction mixture was allowed to stand at room temperature for 2 hours. Excess thionyl chloride was removed leaving the chloride (2) as an oil in near quantitative yield.

EXAMPLE 16

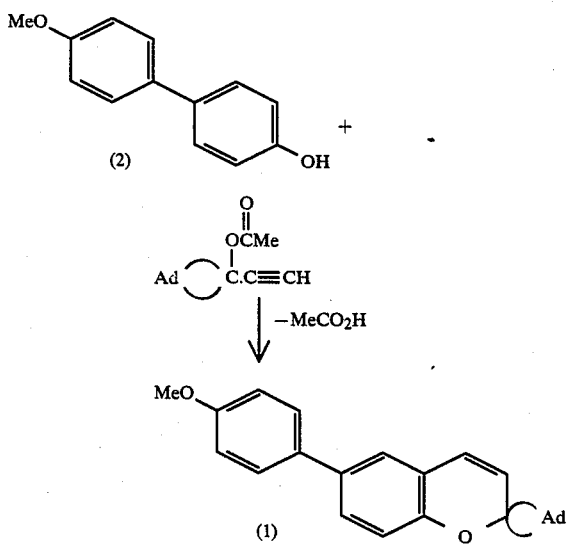

This Example illustrates the preparation of 6-p-methoxyphenyl-HCl by the novel Claisen rearrangement type reaction, using ethynyl adamantanyl acetate and acidic alumina.

Lithium acetylide/ethylene diamine complex (1 part) is added to a stirred solution in tetrahydrofuran of adamantanone (1 part) at a rate such that the temperature is maintained between 60° and 75° C. When the addition is complete, the reaction mixture is stirred at 60° C. for 3 hours, and then poured onto crushed ice (6 to 8 parts). The reaction mixture is extracted with dichloromethane, the organic layer is separated, dried over anhydrous magnesium sulphate, filtered and the solvent removed from the filtrate. The residue is the ethynyl adamantanyl alcohol and was converted to the acetate by reaction with acetyl chloride.

A mixture of p-methoxyphenylphenol (2) (2 g), ethynyl adamantanyl acetate (2 g) and acidic alumina (5 g) was boiled in xylene for 1 hour. Unreacted phenol was recovered. The product contained the desired chromene.

EXAMPLE 17—Preparation of 6-(2' thienyl) HC7T

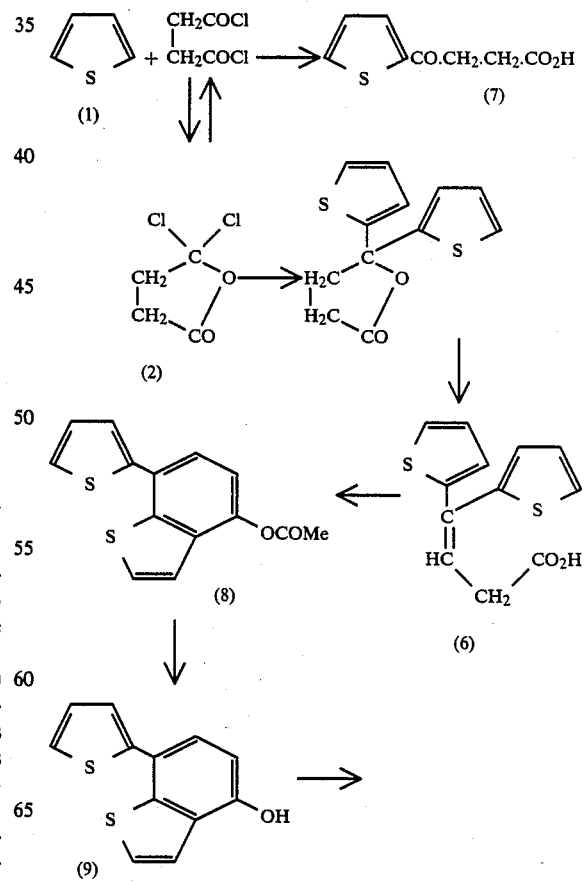

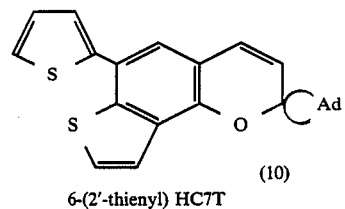

6-(2'-thienyl) HC7T (10)

(a) A mixture of thiophene (1) (36 g) and succinyl chloride (2) (35 g) was added over ½ hour to a suspension of anhydrous aluminium chloride (41.6 g) in ice-cold 1,2-dichloromethane. The reaction mixture was left overnight and poured into water. The organic layer was separated and extracted carefully with dilute sodium carbonate solution. A 3:2 mixture of 4,4-bis(2'-thienyl) but-3-enoic acid (6) and 4-(2'-thienyl)-4-oxobutanoic acid (7) (17.5 g) was obtained. The mixed acids were boiled with anhydrous sodium acetate (5 g) in acetic anhydride (100 cm³) for 6 hours. Acetic anhydride was removed and the residue was extracted with ethanol. Removal of ethanol left the acetate (8) (5 g) which was hydrolysed with ethanolic potassium hydroxide and acidified with hydrochloric acid to give 7-(2'-thienyl) thianaphthen-4-ol (9).

(b) 7-(2'- Thienyl)thianaphthen-4-ol (9) (3.4 g), ethynyl adamantanyl acetate (3.5 g), and alumina (18 g) in xylene (100 cm³) was boiled for 2 hours. The solution showed a heliochromic response to purple which was deeper than for 6-p-methoxyphenyl-9-methoxy HC7, illustrating the colour-deepening influence of the 2'-thienyl group in the 6-position.

The photochromic compounds of this invention can be incorporated into the plastics materials customarily employed for the manufacture of lens. In the case of polyacrylates and methacrylates, such as polymethyl methacrylate (PMMA), the photochromic compound may be included in the polymerisation mixture.

The currently preferred method of incorporating the photochromic compounds into plastics lenses is by solvent imbibition. This procedure involves immersion of the preformed lens in a solution of the heliochromic compound in an inert solvent.

We claim:

1. Photochromic spiro-benzopyrans and spiro-napthopyrans in which a spiro-adamantane group is present in the 2-position of the benzopyran or naphthopyran ring.

2. Photochromatic spiropyrans having the general formula I, II, or III set forth below in which R₃ to R₁₀ independently represent hydrogen, lower alkyl, (1 to 5 carbon atoms), aryl, alkoxy, hydroxy, alkyl- or dialkylamino, halogen or a heterocyclic group, with the proviso that R³ or R⁴ is not hydroxy, alkoxy, or alkyl- or dkalkylamino or in the case of formula I, II, or III the benzene or napthalene ring is benzannelated or annelated with a heterocyclic ring.

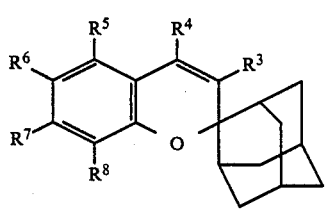
(I)

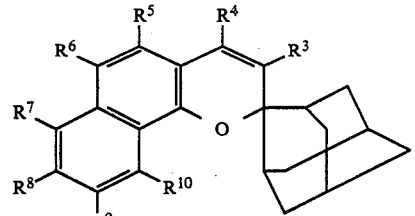
(II)

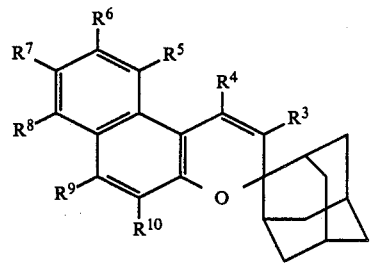
(III)

3. A photochromic spiropyran according to claim 2 wherein the heterocyclic annelated ring is a five or six-membered oxygen or sulphur containing ring.

4. A photochromic spiropyran according to claim 2 having the general formula (II) and which is benzannelated in the R⁵-R⁶ positions.

5. A photochromic spiropyran according to claim 3, having the general formula (I) wherein a fused thiophene, furan or pyrone ring is present in the R⁶-R⁷ or R⁵-R⁶ or R⁷-R⁸ positions.

6. A photochromic spiropyran according to any one of claims 2 to 5, wherein R³-R⁴ are both hydrogen.

7. A photochromic spiropyran according to claim 6, wherein R³ is hydrogen and R⁴ is methyl, phenyl, paramethoxy-phenyl or halogen.

8. A heliochromic spiro-naphthopyran having the following general formula:

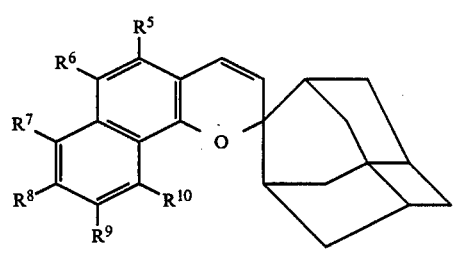

wherein R⁵ to R¹⁰ represent hydrogen, lower alkyl, chlorine, bromine, aryl, hydroxy, alkoxy, alkoxyaryl, alkyl- or dialkylamino, aminoaryl or alkylamino-aryl, or a 5 or 6-membered heterocyclic group or wherein a fused thiophene, furan or pyrone ring is present in the R⁶-R⁷, R⁵-R⁶ or R⁷-R⁸ positions and R⁴ represents hydrogen, alkyl, halogen or an aryl group.

9. A heliochromic spiro-naphthopyran according to claim 8, wherein R⁶ is phenyl, chlorine, para-methoxyphenyl methoxy, thienyl or furyl.

10. A heliochromic spiropyran having the following general formula:

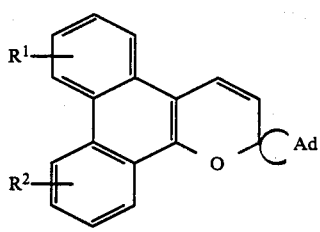

wherein R¹ and R² each represent one or more substituents selected from hydrogen, lower alkyl, halogen, aryl (including substituted aryl), hydroxy, alkyl- or dialkylamino, alkoxy or a heterocyclic group and <Ad represents an adamantane group.

11. A heliochromic spiropyran having the following general formula:

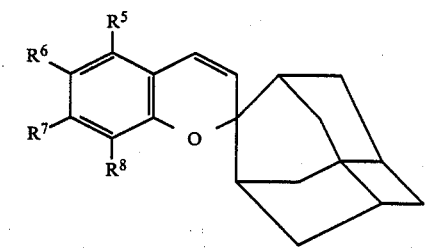

wherein $R^5$ to $R^8$ represent hydrogen, lower alkyl, halogen, alkoxy, alkoxyaryl or a 5 or 6-membered heterocyclic group or $R^6$ and $R^7$ together represent a fused pyrone ring.

* * * * *